United States Patent [19]

Sabara et al.

[11] Patent Number: 5,374,426

[45] Date of Patent: *Dec. 20, 1994

[54] ROTAVIRUS NUCLEOCAPSID PROTEIN VP6 IN VACCINE COMPOSITIONS

[75] Inventors: Marta I. Sabara; Patrick J. Frenchick; Kerry F. Mullin-Ready, all of Saskatoon, Canada

[73] Assignee: University of Saskatchewan, Saskatoon, Canada

[*] Notice: The portion of the term of this patent subsequent to Dec. 10, 2008 has been disclaimed.

[21] Appl. No.: 429,147

[22] Filed: Oct. 30, 1989

Related U.S. Application Data

[63] Continuation of Ser. No. 92,120, Sep. 2, 1987, abandoned, which is a continuation-in-part of Ser. No. 903,222, Sep. 3, 1986, abandoned.

[51] Int. Cl.$^5$ .............................. A01N 25/34
[52] U.S. Cl. ............................ 530/403; 424/186.1; 530/350; 530/324; 530/807; 530/816; 530/402
[58] Field of Search ............... 424/89; 530/350, 403, 530/324, 807, 816; 514/12

[56] References Cited

U.S. PATENT DOCUMENTS

| | | | |
|---|---|---|---|
| 3,906,092 | 9/1975 | Hilleman et al. | 424/89 |
| 4,190,645 | 2/1980 | Almeida | 424/89 |
| 4,341,870 | 7/1982 | Wyatt | 435/237 |
| 4,356,170 | 10/1982 | Jennings | 424/92 |
| 4,459,286 | 7/1987 | Hilleman | 424/87 |
| 4,496,538 | 1/1985 | Gordon | 424/92 |
| 4,571,385 | 2/1986 | Greenberg | 435/172.3 |
| 4,619,828 | 10/1986 | Gordon | 424/92 |
| 4,624,850 | 11/1986 | Albert | 424/89 |
| 4,636,385 | 1/1987 | Plotkin | 424/89 |
| 4,666,886 | 5/1987 | Baschang et al. | 514/18 |
| 4,673,574 | 6/1987 | Anderson | 424/92 |
| 4,695,624 | 9/1987 | Marburg | 530/395 |
| 4,711,779 | 12/1987 | Porro | 424/92 |
| 4,761,283 | 8/1988 | Anderson | 424/92 |
| 4,808,700 | 2/1989 | Anderson | 424/92 |

FOREIGN PATENT DOCUMENTS

| | | |
|---|---|---|
| 0235754 | 9/1987 | European Pat. Off. . |
| 0273366 | 7/1988 | European Pat. Off. . |
| 8505122 | 11/1985 | WIPO . |

OTHER PUBLICATIONS

Organic Chemistry, 3rd Ed., Morrison & Boyd, (1974), p. 1056.
Kapikian et al., *Virology*, pp. 863–906 (1985).
Bastardo et al., (1981) *Infection and Immunity* 34(3):641–7.
Estes et al., (1984) *Nucleic Acids Research* 12(4):1875–1887.
Estes et al., (1984) *Journal of Virology* 61(5):1488–1494.
Bican et al., (1982) *J. of Virology* 43(3):1113–1117.
Buoege et al., (1986) *J. of Virology* 57(1):275–284.
Matsuno et al., (1979) *J. Gen. Virol.* 43:309–316.
Novo et al., (1981) *J. Gen. Virol.* 56:325–335.
Kimura et al., (1987) *Arch. Virol* 92:165–174.
Ready et al., (1987) *Virology* 157:189–198.
Rodger et al., (1977) *J. of Virol.* 24(1):91–98.
Sabara et al., (1985) *J. of Virol.* 53(1):58–66.
Thouless, (1979) *J. Gen. Virol.* 44:187–197.
Dick et al., (1989) *Contributions to Microbiology and Immunology* 10:48–114.
Valenzuela et al., (1985) *Chem. Abstracts 102* number 216278u.
Gorziglia et al., (1985) *Chem. Abstracts 103* No. 156990d.
Valenzuela et al., (1986) *Chem. Abstracts 104* No. 223449u.
Pett et al., (1975) *Chem. Abstracts 82* No. 135382q.
Tanaguchi et al., (1986) *Chem Abstracts 104* No. 107585n.
Sandino et al., (1986) *Chem Abstracts 105* No. 205956z.
Killen et al., (1982) *Chem. Abstracts 97* No. 196630a.
Gerald et al., (1984) *Chem. Abstracts 101*, No. 144949t.

*Primary Examiner*—Robert J. Hill, Jr.
*Assistant Examiner*—T. D. Wessendorf
*Attorney, Agent, or Firm*—Morrison & Foerster

[57] ABSTRACT

Immunological carrier complexes are provided utilizing the VP6 polypeptide from rotavirus as the carrier molecule. Also provided are methods of binding epitope-bearing molecules (e.g., haptens) to the VP6 carrier molecule through binding peptides. The VP6 carrier can be a VP6 monomer, oligomer, or a particle.

16 Claims, 9 Drawing Sheets

FIG. 1

```
                       MET ASP VAL LEU TYR SER LEU SER LYS THR LEU LYS ASP ALA   14
5'- GGCTTTTAAACGAAGTCTTCAAC ATG GAT GTC CTA TAC TCT TTG TCA AAG ACT CTT AAA GAC GCT   65

ARG ASP LYS ILE VAL GLU GLY THR LEU TYR SER ASN VAL SER ASP LEU ILE GLN GLN PHE    34
AGA GAC AAA ATT GTC GAA GGC ACA TTG TAT TCT AAC GTG AGT GAT CTA ATT CAA CAA TTT   125

ASN GLN MET ILE ILE THR MET ASN GLY ASN GLU PHE GLN THR GLY GLY ILE GLY ASN LEU    54
AAT CAA ATG ATA ATT ACT ATG AAT GGA AAT GAA TTT CAA ACT GGA GGA ATC GCT AAT TTG   185

PRO ILE ARG ASN TRP ASN PHE ASN PHE GLY LEU LEU GLY THR THR LEU LEU ASN LEU ASP    74
CCA ATT AGA AAC TGG AAT TTT AAT TTC GGG TTA CTT GGA ACA ACT TTG CTG AAC TTA GAC   245

ALA ASN TYR VAL GLU THR ALA ARG ASN THR ILE ASP TYR PHE VAL ASP PHE VAL ASP ASN    94
GCT AAT TAT GTT GAA ACG GCA AGA AAT ACA ATT GAT TAT TTC GTG GAT TTT GTA GAC AAT   305

VAL CYS MET ASP GLU MET VAL ARG GLU SER GLN ARG ASN GLY ILE ALA PRO GLN SER ASP   114
GTA TGC ATG GAT GAG ATG GTT AGA GAA TCA CAA AGG AAC GGA ATT GCA CCT CAA TCA GAC   365

SER LEU ARG LYS LEU SER ALA ILE LYS PHE LYS ARG ILE ASN PHE ASP ASN SER SER GLU   134
TCC CTA AGA AAG CTG TCA GCC ATT AAA TTC AAA AGA ATA AAT TTT GAT AAT TCG TCG GAA   425

TYR ILE GLU ASN TRP ASN LEU GLN ASN ARG ARG GLN ARG THR GLY PHE THR PHE HIS LYS   154
TAC ATA GAA AAC TGG AAT TTG CAA AAT AGA AGA CAG AGG ACA GGT TTC ACT TTT CAT AAA   485

PRO ASN ILE PHE PRO TYR SER ALA SER PHE THR LEU ASN ARG SER GLN PRO ALA HIS ASP   174
CCA AAC ATT TTT CCT TAT TCA GCA TCA TTT ACA CTA AAT AGA TCA CAA CCC GCT CAT GAT   545

ASN LEU MET GLY THR MET TRP LEU ASN ALA GLY SER GLU ILE GLN VAL ALA GLY PHE ASP   194
AAT TTG ATG GGC ACA ATG TGG TTA AAC GCA GGA TCG GAA ATT CAA GTC GCT GGA TTT GAC   605

TYR SER CYS ALA ILE ASN ALA PRO ALA ASN ILE GLN GLN PHE GLU HIS ILE VAL PRO LEU   214
TAC TCA TGT GCT ATT AAC GCA CCA GCC AAT ATA CAA CAA TTT GAG CAT ATT GTG CCA CTC   665

ARG ARG VAL LEU THR THR ALA THR ILE THR LEU LEU PRO ASP ALA GLU ARG PHE SER PHE   234
CGA AGA GTG TTA ACT ACA GCT ACG ATA ACT CTT CTA CCA GAC GCG GAA AGG TTT AGT TTT   725

PRO ARG VAL ILE ASN SER ALA ASP GLY ALA THR THR TRP PHE PHE ASN PRO VAL ILE LEU   254
CCA AGA GTG ATC AAT TCA GCT GAC GGC GCA ACT ACA TGG TTT TTC AAC CCA GTG ATT CTC   785

ARG PRO ASN ASN VAL GLU VAL GLU PHE LEU LEU ASN GLY GLN ILE ILE ASN THR TYR GLN   274
AGG CCG AAT AAC GTT GAA GTG GAG TTT CTA TTG AAT GGA CAG ATA ATA AAC ACT TAT CAA   845

ALA ARG PHE GLY THR ILE VAL ALA ARG ASN PHE ASP THR ILE ARG LEU SER PHE GLN LEU   294
GCA AGA TTT GGA ACT ATC GTA GCT AGA AAT TTT GAT ACT ATT AGA CTA TCA TTC CAG TTA   905

MET ARG PRO PRO ASN MET THR PRO ALA VAL ALA VAL LEU PHE PRO ASN ALA GLN PRO PHE   314
ATG AGA CCA CCA AAC ATG ACA CCA GCA GTA GCA GTA CTA TTC CCG AAT GCA CAG CCA TTC   965

GLU HIS HIS ALA THR VAL GLY LEU THR LEU ARG ILE GLU SER ALA VAL CYS GLU SER VAL   334
GAA CAT CAT GCA ACA GTG GGA TTG ACA CTT AGA ATT GAG TCT GCA GTT TGT GAG TCT GTA  1025

LEU ALA ASP ALA SER GLU THR LEU LEU ALA ASN VAL THR SER VAL ARG GLN GLU TYR ALA   354
CTC GCC GAT GCA AGT GAA ACT CTA TTA GCA AAT GTA ACA TCC GTT AGG CAA GAG TAC GCA  1085

ILE PRO VAL GLY PRO VAL PHE PRO PRO GLY MET ASN TRP THR ASP LEU ILE THR ASN TYR   374
ATA CCA GTT GGA CCA GTC TTT CCA CCA GGT ATG AAC TGG ACT GAT TTA ATC ACC AAT TAT  1145

SER PRO SER ARG GLU ASP ASN LEU GLN ARG VAL PHE THR VAL ALA SER ILE ARG SER MET   394
TCA CCG TCT AGG GAG GAC AAT TTG CAA CGC GTA TTT ACA GTG GCT TCC ATT AGA AGC ATG  1205

LEU ILE LYS ***                                                                   397
CTC ATT AAA TGA GGACCAAGCTAACAACTTGGTATCCAACTTTGGTGAGTATGTAGCTATATCAAGCTGTTTGAA  1280

CTCTGTAAGTAAGGATGCGTATACGCATTCGCTACACTGAGTTAATCACTCTGATGGTATAGTGAGAGGATGTGACC-3' 1357
```

FIG. 5
ASSEMBLY OF VP6 MONOMER INTO VARIOUS OLIGOMERIC STRUCTURES
MONOMER (45k)
↓ Nonconvalent Interaction
TRIMER (135k)
 ⟶ SMALL-HOLE LATTICE
↓ Intermolecular Disulphide Bridging
TRIMERIC PAIR (270k)
↓ Intermolecular Disulphide Bridging
HMW Aggregate (HEXAMER)
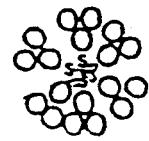
⟶ TUBES
⟶ SPHERES
⟶ SMALL HEXAGONAL LATTICE
DIMER (artifact)

ROTAVIRUS NUCLEOCAPSID PROTEIN VP6 IN VACCINE COMPOSITIONS

CROSS-REFERENCE TO RELATED APPLICATIONS

This application is a continuation of Ser. No. 092,120, filed Sep. 2, 1987, now abandoned which is a continuation-in-part of Ser. No. 903,222, filed Sep. 3, 1986, now abandoned.

TECHNICAL FIELD

The present invention relates to immunological carriers and vaccine compositions. More particularly, the present invention relates to the use of rotavirus inner capsid protein VP6 as an immunologic carrier, as well as its use in a vaccine composition for use in stimulating immunity against rotavirus infections.

BACKGROUND OF THE INVENTION

Rotavirus is a genus of the family Reoviridae. This genus of viruses is widely recognized as the major cause of gastroenteritis of infants and young children in most areas of the world. In the lesser developed countries diarrheal diseases such as gastroenteritis constitute a major cause of mortality among infants and young children. For a general background on rotoviruses, see Kapikian et al., in *Virology*, pp. 863-906 (B. N. Fields et al., eds., 1985), the disclosure of which is incorporated herein by reference.

Immunity to rotavirus infections and illness has been poorly understood. Animal studies, however, have been conducted directed to the relative importance of systemic and local immunity. Bridger et al. (1981) Infect. Immun. 31:906-910; Lecce et al. (1982) J. Clin. Microbiol. 16:715-723; Little et al. (1982) Infect. Immun. 38:755-763. For example, it has been observed that calves develop a diarrheal illness despite the presence of serum rotavirus antibody at the time of infection. Calves which are fed colostrum-containing rotavirus antibodies immediately before and after infection with rotavirus, however, do not develop diarrhea within the normal incubation period. See, e.g., Bridger et al. (1975) Br. Vet. J. 131:528-535; Woode et al. (1975) Vet. Rec. 97:148-149. Similar results have been achieved with newborn lambs, who developed resistance when fed colostrum or serum containing rotavirus antibodies for several days during which period the lambs were challenged with rotavirus. Snodgrass et al. (1976) Arch. Virol. 52:201-205.

In studies of the effect of administering rotavirus to humans, it was found that a preexisting high titer of serum neutralizing antibodies to rotavirus correlated with resistance to diarrheal illness. Kapikian et al. (1983) Dev. Biol. Standard 53:209-218; Kapikian et al. (1983) J. Infect. Dis. 147:95-106. In infants and children, however, the presence of serum antibody to rotavirus has not been associated with resistance to infection or illness. See, e.g., Black et at.. (1982) J. Infect. Dis. 145:483-489; Gurwith et al. (1981) J, Infect. Dis. 144:218-224; McLean et al. (1981) J. Clin. Microbiol. 13:22-29.

Most current efforts in experimental rotavirus immunoprophylaxis are aimed at the development of live attenuated virus vaccines. Attenuation, however, is usually associated with a decrease in the level of viral replication in the target organ; i.e., the epithelium the small intestine. Attenuated mutants of other mucosal viruses, however, have exhibited a diminished immune response correlated with the decrease in replication. Since the protective efficacy of wild-type virus infection is marginal, it may be impossible to achieve the desired immunoprophylaxis with a mutant exhibit decreased replication. Two bovine rotaviruses, NCDV and the UK strain, have been produced in attenuated form and evaluated as vaccines in humans. Vesikari et al. (1983) Lancet 2:807-811; Vesikari et al. (1984) Lancet 1:977-981; Wyatt et al. (1984) in Conference Proceedings: Control and Eradication of Infectious Diseases in Latin America.

Another approach to the development of an attenuated rotavirus vaccine is based on the ability of rotaviruses to undergo gene reassortment during coinfection. A number of "hybrid" strains have been isolated from cultures coinfected with a wild-type animal rotavirus and a human rotavirus. Strains are selected which receive the gene coding for the outer nuclear capsid protein VP7, the remaining genes being derived from the animal rotavirus parent. See, e.g., *Immunogenicity*, pp. 319-327 (Chanock & Lerner, eds., 1984).

Still another approach to immunization has been the suggestion of using recombinantly produced VP7 polypeptide in a vaccine. See, e.g., *Virology*, p. 892 (B. N. Fields et al., eds., 1985). It has been further suggested, however, that recombinant VP7 is unlikely to produce an effective primary local intestinal immune response. Id. at 893. The VP7 gene from several strains of rotavirus has been cloned and full-length or near full-length cDNA has been attained. See, e.g., Arias et al. (1984) J. Virol. 50:657-661; Both et al. (1983) Proc. Natl. Acad. Sci. USA 80:3091-3095; Elleman et al. (1983) Nucleic Acid Res. 11:4689-4701; Flores et al. in *Modern Approached to Vaccines; Molecular and Chemical Basis of Virus Virulence and Immunogenicity*, pp. 159-164 (R. M. Chanock et al., eds., 1983).

It has also been suggested that synthetic peptides corresponding to major anogenic sites of VP7 may be useful in immunization. *Virology*, supra, p. 893. In addition, passive immunization with rotavirus antibodies has been shown to be effective in preventing rotavirus illness in animals and in infants and young children. Id.

The most abundant structural protein in rotavirus particles is the approximate 45K MW nucleocapsid or inner capsid protein coded for by gene known in the art as virus protein 6 or VP6. Although not an integral component of the outer capsid, it is an important viral antigen. It has been identified as the subgroup antigen by using several techniques including complement fixation, ELISA, immunoadherence agglutination assay, and specific monoclonal antibodies. VP6 is also described as the common rotavirus group antigen since some monoclonal antibodies against it will react with all rotaviruses, and polyclonal serum raised against a single rotavirus type can detect most other rotavirus strains. Aside from its antigenic properties, VP6 is very immunogenic and several investigators have found that polyclonal serum raised to this protein has neutralizing ability. Bastardo et al. (1981) Infect. & Immun. 34:641-647.

The gene encoding VP6 has been cloned. See, e.g., Estes et al. (1984) Nucleic Acids Res. 12:1875-1887. VP6 has also been produced by recombinant methods. Estes et al. (1987) J. Virol. 61:1488-1494.

Vaccine compositions for rotavirus disease comprised of peptides from VP7, VP6 and VP3 have also been proposed. See commonly owned patent applications: U.S. Ser. No. 903,325 (filed Sep. 3, 1986); Canadian Ser. No. 526,116 (filed Dec. 23, 1986); Australian Ser. No. 66987/86 (filed Dec. 24, 1986); Chinese Ser. No. 86108975 (filed Dec. 25, 1986); EPO Ser. No. 117 981.0 (Dec. 23, 1986); and Japanese Ser. No. 61-308945 (filed Dec. 26, 1986), the disclosures of which are incorporated by reference herein.

Several immunologic carriers are known in the art, including, but not limited to, keyhole limpet hemocyanin (KLH), bovine serum albumin (BSA), ovalbumin (OVA), beta-galactosidase (B-GAL), penicillinase, poly-DL-alanyl-poly-L-lysine, and poly-L-lysine. The coupling of the desired hapten or other epitope-bearing molecule to such carriers often requires elaborate chemical procedures. Such procedures are expensive and may have a deleterious effect on the final complex comprised of the carrier and epitope-bearing molecule. Thus, there is a need in the art for improved immunological carriers to which epitope-bearing molecules can be attached readily, but which are also at least as effective as prior art immunologic carriers.

SUMMARY OF THE INVENTION

The present invention is based on the discovery that VP6 polypeptides of rotaviruses, or functional fragments thereof, in either monomeric or oligomeric forms, have the ability to bind peptides by virtue of an interaction between the peptide and binding site(s) on the VP6 polypeptide to form a VP6 - binding peptide complex. The present invention is also based on the discovery that VP6, in its monomeric or oligomeric forms, can be advantageously employed as an immunologic carrier to which molecules bearing an epitope of interest can be attached. Preferably, these epitope-bearing molecules can be attached to the VP6 polypeptide by use of a binding peptide. The above discoveries, therefore, provide for the production of compositions which can be used to stimulate an immune response to VP6, VP6 complex with an epitope-bearing molecule, as well as to the binding peptide if it is employed in the complex.

In one embodiment, the present invention is directed to a composition capable of raising an immunological response in a mammal to a selected epitope comprising an immunological carrier complex, said complex comprised of an epitope-bearing molecule expressing said selected epitope, said epitope-bearing molecule being selected from the group consisting of polypeptides, carbohydrates and nucleic acids; said epitope-bearing molecule being coupled to a carrier protein selected from the group consisting of monomers and oligomers of a polypeptide homologous to a rotavirus VP6 inner capsid protein amino acid sequence.

In several preferred embodiments of the above composition, the epitope-bearing molecule is a polypeptide, and the carrier protein is a VP6 inner capsid protein. In particularly preferred embodiments, the VP6 carrier protein is an oligomer formed into a particle, such as a tube or sphere. In a still further preferred embodiment, the epitope-bearing molecule is coupled to the carrier protein through a protein-protein interaction with a binding peptide specific for the VP6 binding site(s).

In another embodiment of the present invention, an improved vaccine composition is provided wherein the epitope of interest is on a polypeptide bound to a carrier protein, the improvement comprising using rotavirus VP6 inner capsid polypeptide as said carrier protein.

In other embodiments of the present invention, vaccination methods are provided, as well as specific binding peptides.

Further embodiments of the present invention will readily occur to those of ordinary skill in the

BRIEF DESCRIPTION OF THE DRAWINGS

FIG. 1 shows the nucleotide sequence of a cloned copy of the rotavirus strain S-A11 gene 6 encoding the polypeptide VP6. The sense strand (corresponding to the mRNA) is shown, as well as the predicted amino acid sequence of VP6. Termination sites are underlined. See Estes et al. (1984) Nucleic Acids Res. 12:1875–1887.

FIG. 5 is a schematic representation of the assembly of VP6 monomer into various oligomeric structures.

DETAILED DESCRIPTION

Figure 2A:
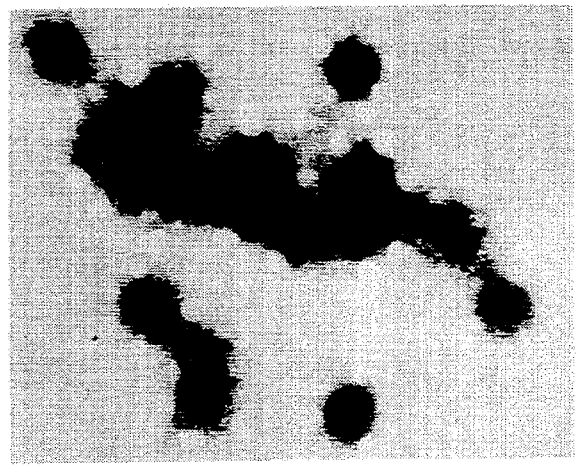
FIG. 2 shows electron micrographs of particles produced from reassembled rotavirus VP6. Panel A shows particles from VP6 isolated from human strain WA rotavirus (subgroup 2), and panel B shows particles reassembled from recombinantly produced VP6 from a baculovirus expression system.

In describing the present invention, the following terms will be employed, and are intended to be defined as indicated below.

An "immunological response" to an epitope of interest is the development in a mammal of either a cell- or antibody-mediated immune response to the epitope of interest. Usually, such a response consists of the mammal producing antibodies and/or cytotoxic T cells directed specifically to the epitope of interest.

An "immunological carrier complex" refers to a chemical complex between an immunologic carrier molecule, usually a protein, and a hapten or other epitope-bearing molecule. The epitope on the hapten or other epitope-bearing molecule for which an immunological response is desired is referred to as the "epitope of interest" or the "selected epitope".

An "epitope-bearing molecule" refers to a molecule within an immunological carrier complex which bound to the carrier molecule and bears the epitope interest. The epitope-bearing molecule of the present invention can include, but is not limited to, polypeptides, carbohydrates, nucleic acids, and lipids. Further examples are given below.

A "rotavirus VP6 inner capsid protein" refers the art-recognized major viral protein of the inner capsid from any species or strain within the genus Rotavirus. See, e.g., Kapikian et al., supra. Examples of rotavirus strains from which the VP6 protein can be isolated and employed in the present invention include, but are not limited to, Simian SA-11, human D rotavirus, bovine UK rotavirus, human Wa or W rotavirus, human DS-1 rotavirus, rhesus rotavirus, the "O" agent, bovine NCDV rotavirus, human K8 rotavirus, human KU rotavirus, human DB rotavirus, human S2 rotavirus, human KUN rotavirus, human 390 rotavirus, human P rotavirus, human M rotavirus, human Walk 57/14 rotavirus, human Mo rotavirus, human Ito rotavirus, human Nemoto rotavirus, human YO rotavirus, human McM2 rotavirus, rhesus monkey MMU18006 rotavirus, canine CU-1 rotavirus, feline Taka rotavirus, equine H-2 rotavirus, human St. Thomas No. 3 and No. 4 rotaviruses, human Hosokawa rotavirus, human Hochi rotavirus, porcine SB-2 rotavirus, porcine Gottfried rotavirus, porcine SB-1A rotavirus, porcine OSU rotavirus, equine H-1 rotavirus, chicken Ch.2 rotavirus, turkey Ty.1 rotavirus, and bovine C486 rotavirus. Thus, the present invention encompasses the use of VP6 from any rotavirus strain, whether from subgroup I, subgroup II, or any as yet unidentified subgroup, as well as from any of the serotypes 1-7, as well as any as yet unidentified serotypes. Furthermore, the present invention encompasses the use as an immunologic carrier of polypeptides having homologous amino acid sequences to rotavirus VP6 amino acid sequences which are unique to the class, or any member of the class, of VP6 polypeptides. Such unique sequences of VP6 proteins are referred to as a "rotavirus VP6 inner capsid protein amino acid sequence".

"Oligomers" refer to multimeric forms of, for example, VP6 polypeptides. Usually, such VP6 oligomers are trimers formed by intermolecular disulfide bridging between VP6 monomers. See, e.g., FIG. 5.

The binding of an epitope-bearing molecule to a VP6 carrier protein through "protein-protein interaction(s)" refers to the type of chemical binding, both covalent and non-covalent, between a binding peptide region of the epitope-binding molecule and the VP6 carrier molecule. The exact nature of this binding is not understood. It is characterized, however, as the binding phenomenon observed when a peptide, having a Cys and another charged amino acid (e.g., Arg) in a structural relationship to each other analogous to that shown in peptide A or B (below), binds to VP6 binding sites on the carrier molecule through mere mixing of VP6 carrier protein and molecules containing the binding peptide region. It is believed that this protein-protein interaction is a combination of a disulfide bridge involving the Cys, and a non-covalent interaction involving the charged amino acid, but applicants do not wish to be bound by this theory.

A "binding peptide" refers to amino acid sequences which have the ability to bind through a protein-protein interaction with a VP6 polypeptide. These binding peptides are discussed in more detail below.

A composition "free of rotavirus virions" refers to a composition which does not contain intact virus particles, although it may contain particles formed from VP6 complexed to other molecules.

A "vaccine composition", according to the present invention, is an otherwise conventional vaccine formulation employing either VP6 polypeptides alone or in an immunological carrier complex as the active ingredient. The preparation of vaccines containing the above active ingredients is well understood in the art. Typically, vaccines are prepared as injectables, either as liquid solutions or suspensions; solid forms suitable for solution in, or suspension in, liquid prior to injection may also be prepared. The preparation may also be emulsified or the active ingredient encapsulated in liposomes. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Injectable vaccine formulations will contain an effective amount of the active ingredient, the exact amount being readily determined by one skilled in the art. The active ingredient can range from about 1% to about 95% (w/w) of the injectable composition, or even higher or lower if appropriate.

Additional vaccine formulations which are suitable for other modes of administration include suppositories and, in some cases, oral formulation. For suppositories, the vaccine composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral formulations include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Furthermore, the VP6 proteins or immunological carrier complexes of the present invention may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine composition of the present invention may be administered in a manner compatible with the dosage formulation, and in such amounts as will be therapeutically effective and immunogenic. The quantity to be administered depends on the subject to be treated, the capacity of the subjects immune system to synthesize antibodies, and the degree of protection desired. Precise amounts of active ingredient desired to be administered depend on the judgment of the practitioner and are peculiar to each subject. The establishment of effective dosages for a particular formulation, however, are within the skill of the art through routine trials establishing dose-response curves.

The rotavirus genome consists of eleven segments of double-stranded RNA. These 11 genes encode for the production of at least six structural proteins of the virus. In complete virus particles, these six proteins occur in a double-shelled arrangement. There are three inner shell (capsid) proteins designated virus protein (VP) 1, 2, and 6. There are three outer capsid proteins, two of which are designated VP3 and VP7. The third outer capsid protein, which is encoded by genomic segment 10 or 11, has not yet been assigned a number. The molecular weights of these proteins are shown in Table 1.

TABLE 1

Gene assignment and Molecular Weight of the Major Rotavirus Structural Proteins

| Genomic Segment | Protein Designation | Molecular Weight | Location* |
|---|---|---|---|
| 1 | VP1 | 110K | inner |
| 2 | VP2 | 92K | inner |
| 4 | VP3 | 84K | outer |
| 6 | VP6 | 45K | inner |
| 7 8 triplet 9 | VP7 | 41K | outer |
| 10 or 11 | ND | 20K | outer |

*Designates location of the structural protein in the inner or outer capsid of complete rotavirus particles.

In different rotaviruses, the absolute order of the genomic segments does not always correspond to the same genes. For example, the electrophoretic order of segments 7, 8, and 9 changes among rotaviruses from different animal species. This is referred to as inversion or "flip-flopping" of genome segments. The gene triplet formed by segments 7, 8, and 9 codes for three polypeptides, the neutralization-specific major outer capsid glycoprotein identified as virus protein (VP) 7 and two nonstructural proteins which are not shown in the table. In rotavirus strains SA-11, W, and Wa, gene 9 codes for VP7. In rotavirus strain DS-1 and UK bovine rotavirus, however, gene 8 codes for VP7. There are discrepancies in the literature about the exact molecular weight of VP7, as well as of other rotavirus proteins. Several researchers have suggested that this is in part due to the many variations in methods used to: (1) separate the individual polypeptides, (2) prepare virus samples for electrophoresis, (3) detect polypeptides in polyacrylamide gels, and (4) detect various post-translational modifications of primary gene products. In addition, especially for bovine and human rotavirus, there are variations in the mobility of proteins derived from different isolates originating from the same species. The molecular weights shown in Table 1 are those reported by Sabara et al. (1985) J. Virol. 53:58–66.

As discussed above, VP6 is the most abundant of the inner capsid proteins, constituting about 80% by weight of the inner shell. Rotaviruses can be divided into two subgroups (I or II) based on an epitope on VP6 which can be identified using monoclonal antibodies. Most rotaviruses examined to date fall into one of the two subgroups; however, there is evidence that both subgroup epitopes can be located on a single VP6 molecules. For example, recently an equine rotavirus was identified as having both subgroup 1 and 2 epitopes on VP6. See, e.g., Hoshino et al. (1987) Virology 157:488–496. Therefore, it is not inconceivable that the subgrouping classification may be extended or modified as new isolates are identified and their genes sequenced. There are also at least 7 serology groups into which rotaviruses have been classified.

All VP6 molecules sequenced to date consist of 397 amino acids, although some variability in the molecular weight of the protein has been reported which may indicate a protein with more or less than this number of amino acids. Specifically, the reported molecular weight range for VP6 is 41–45K, thereby indicating an amino acid size range of 397–425. However, molecular weight variability does not necessarily reflect a difference in the number of amino acids but can be due to electrophoretic conditions used in characterization of the protein. Only by sequencing the gene coding for a particular VP6 can the number of amino acids be determined (See, e.g., FIG. 1). The amino acid homology between VP6s belonging to the two different subgroups is 80% or more, based on the VP6 genes sequenced to date.

Within rotavirus, monomeric units of VP6 exist in a variety of oligomeric forms. Trimeric units (molecular weight about 135K) occur in both the virus particle and in infected cells, with the intersubunit linkage consisting of non-covalent interactions. These trimeric units complex further by virtue of disulfide bridges into larger units which likely represent the ring-like structures observed using electron microscopy. By employing different sample buffers, these nucleocapsid oligomeric complexes can be visualized on polyacrylamide gels.

VP6 protein can be prepared by any of several methods. First, VP6 can be purified from in vitro-derived single-shelled virus particles by calcium chloride ($CaCl_2$) or lithium chloride (LiCl) treatment by standard techniques. See, e.g., Almeida et al. (1979) J. Med. Virol. 4:269–277; Bican et al. (1982) J. Virol. 43:1113–1117; Gorziglia et al. (1985) J. Gen. Virol. 66:1889–1900; Ready et al. (1987) Virology 157:189–198. Alternatively, VP6 can be produced by recombinant DNA techniques, which are fully explained in the literature. See, e.g., Maniatis, Fritsch & Sambrook, *Molecular Cloning: A Laboratory Manual* (1982); *DNA Cloning*, Volumes I and II (D. N. Glover ed. 1985); *Oligonucleotide Synthesis* (M. J. Gait 1984); *Nucleic Acid Hybridization* (B. D. Hames & S. J. Higgins eds. 1985); Transcription and Translation (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984).

DNA coding sequences encoding VP6 polypeptides can be derived from VP6 mRNA. See, e.g., Estes et al., supra; Both et al. (1984) J. Virol. 51:97–101; Cohen et al. (1984) Virology 138:178–182. Alternatively, a DNA sequence encoding VP6 can be prepared synthetically rather than cloned. The DNA sequence can be designed with the appropriate codons for a VP6 amino acid sequence. In general, one will select preferred codons for the intended host if the sequence will be used for expression. The complete sequence is assembled from overlapping oligonucleotides prepared by standard methods and assembled into a complete coding sequence.. See, e.g., Edge (1981) Nature 292:756; Nambair et al. (1984) Science 223:1299; Jay et al. (1984) J. Biol. Chem. 259:6311.

Once a coding sequence for VP6 has been prepared or isolated, it can be cloned into any suitable vector or replicon. Numerous cloning vectors are known to those of skill in the art, and the selection of an appropriate cloning vector is a matter of choice. Example of recombinant DNA vectors for cloning and host cells which they can transform include the bacteriophage lambda (E. coli), pBR322 (E. coli), pACYC177 (E. coli), pKT230 (gram-negative bacteria), pGV1106 (gram-negative bacteria), pLAFR1 (gram-negative bacteria), pME290 (non-E. coli gram-negative bacteria), pHV14 (E. coli and Bacillus subtilis), pBD9 (Bacillus), pIJ61 (Streptomyces), pUC6 (Streptomyces), YIp5 (Saccharomyces), YCp19 (Saccharomyces) and bovine papilloma virus (mammalian cells). See generally, DNA Cloning: Vols. I & II, supra; T. Maniatis et al., supra; B. Perbal, supra.

The coding sequence for VP6 can be placed under the control of a promoter, ribosome binding site (for bacterial expression) and, optionally, an operator (collectively referred to herein as "control" elements), so that the DNA sequence encoding VP6 is transcribed into RNA in the host cell transformed by a vector containing this expression construction. The coding sequence may or may not contain a signal peptide or leader sequence. bacteria, for example, VP6 is preferably made by the expression of a coding sequence containing a leader sequence which is removed by the bacterial host in post-translational processing. See, e.g., U.S. Pat. Nos. 4,431,739; 4,425,437; 4,338,397.

An expression vector is constructed so that the VP6 coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, VP6 is produced by growing host cells transformed by an expression vector described above under conditions whereby the VP6 protein is expressed. The VP6 protein is then isolated from the host cells and purified. If the expression system secretes the VP6 into growth media, the protein can be purified directly from cell-free media. If the VP6 protein is not secreted, it is isolated from cell lysates. The selection of the appropriate growth conditions and recovery methods are within the skill of the art.

Purified VP6 protein exhibits structural polymorphism. Specifically m hexamers and small hexagonal lattices are present in many of the samples. Tubular particles form between about pH 5.0 and about pH 9.0, and are moderately stable to changes in temperature and ionic strength. The formation of these particles is gully reversible. Spherical particles reassembling single-shelled virus can be formed at about pH 4.0. A novel structure, in the form of sheets, composed of small-hole lattice, is formed in samples shifted from about pH 6.0 to about pH 4.0. These results demonstrate the importance of VP6 and of protein-protein interactions for rotavirus assembly.

Such protein-protein interactions are likely involved in the observed phenomenon that certain peptines can bind to VP6 in its monomeric form or to various oligomeric structures formed from VP6 monomers, such as in vitro assembled tubes and spheres. The attachment is mediated by a specific binding site(s) within VP6. The structures which result from this binding, i.e., VP6 with a bound peptide, shall be referred to as VP6 binding peptide complexes. They can function as carriers to which other molecules bearing an epitope of interest (e.g., haptens) can be attached. By definition, therefore, VP6 bound to another molecule by virtue of a specific amino acid sequence (binding peptide), which occurs naturally or has been tailored onto the epitope-bearing molecule, can be defined as an immunologic carrier for such a molecule.

Many molecules are known in the art that bear an epitope and which can be useful when attached to a carrier. Examples of the classes of such molecules, usually macromolecules, are polypeptides, carbohydrates, and nucleic acids. Proteins, glycoproteins, and peptides can include cytokines, hormones, glucagon, insulin-like growth factors, growth hormone, thyroid stimulating hormone, prolactin, inhibin, secretin, neurotensin, cholecystokinin or fragments thereof, calcitonin, somatostatin, thymic hormones, neurotransmitters and blockers, peptide-releasing factors (e.g., enkephalins), growth hormone releasing factor, as well as antigenic fragments of proteins, such as calmodulin, E. coli heat stable and heat labile enterotoxin, cholera toxin; and enzymes, such as protein kinase of Rous sarcoma virus. Examples of nucleotides include polynucleotide fragments, restrictions enzyme sites, and cyclic nucleotides (e.g., cyclic adenosine monophosphate). Examples of carbohydrates and carbohydrate complexes include bacterial capsules or exopolysaccharides (e.g., from Hemophilus influenzae B), bacterial lipid A associated core antigens (e.g., from Pseudomonas species), blood group antigens (e.g., the ABO antigens), and glycolipids. Examples of lipids include fatty acids, glycerol derivatives, prostaglandins (e.g., prostaglandin $E_2$), and lipopeptides (e.g., leukoteiene $B_4$). Molecules of interest can also include alkaloids, such as vindoline, serpentine, catharanthine, steroid hormones, such as testosterone, estradiol, aldosterone, endrostenedione, or fragments thereof, as well as vitamins containing OH, NH, SH, CHO, or COOH functional groups.

In order to attach molecules to VP6 carriers, one may employ conventional chemical coupling techniques. A particular advantage of the VP6-binding peptide complex as a carrier, however, is that this system facilitates the attachment of molecules with minimal manipulation. For example, a synthetic peptide corresponding to an antigenic or immunogenic region of a particular infectious agent (the epitope of interest) can be chemically synthesized in such a way that it also contains the amino acid sequence (binding peptide) necessary to link it to VP6. This can be done without altering the antigenicity of the region to which immune responses are sought and may enhance the immunogenicity of this region. The antigenic region can also be produced via recombinant DNA technology, as describe above, in which case the nucleotide sequence corresponding to the binding peptide can be added so that the resulting product is a combination (fusion protein) of the antigenic region and the binding peptide. Attachment of the molecule to the VP6 carrier is then simply achieved by mixing the two substances without additional manipulation.

Several peptides have been found or designed that bind to VP6. The amino acid sequences for two are:
  (1) Peptide A (22 amino acids): Cys-Asp-Gly-Lys-Tyr-Phe-Ala-Tyr-Lys-Val-Glu-Thr-Ile-Leu-Lys-Arg-Phe-His-Ser-Met-Tyr-Gly, and
  (2) Peptide B (25 amino acids): Cys-Asn-Ile-Ala-Pro-Ala-Ser-Ile-Val-Ser-Arg-Asn-Ile-Val-Tyr-Thr-Arg-Ala-Gin-Pro-Asn-Gln-Asp-Ile-ala.

Both peptides A and B occur naturally as portions of virus protein 3 (VP3) of rotaviruses and are sensitive to trypsin. Cleavage of the peptides by trypsin prevents them from binding to VP6. It is clear that both of the sequences which are given herein are by way of example only, and that other compositions related to binding sequences, or sequences in which limited conservative amino acid changes are introduced, can also be used. Indeed, as described below, additional binding peptides can be designed by those of skill in the art in light of the present disclosure. For example, variant peptides derived from peptide B were further investigated in order to delineate the features of the peptide which are important for binding to VP6. The features relate to the spatial arrangement of a cysteine and arginine residue, and the three-dimensional conformation of a peptide which allows it to bind to VP6. Therefore, any peptide which exhibits these characteristics can be considered as a binding peptide.

Below are examples of specific embodiments for carrying out the present invention. The examples are offered for illustrative purposes only, and are not intended to limit the scope of the present invention in any way.

EXAMPLES

1. Production of VP6

A. Isolation of Native VP6

Bovine rotavirus isolate C486 was propagated and purified as previously described. Sabara et al. (1986) J. Gen. Virol. 68:123-133. Briefly, virus was grown in confluent African monkey kidney cells (MA-104) ill the absence of fetal bovine serum and in the presence of 10 ug trypsin/ml. Virus was purified by differential centrifugation and pelleted for 2 hours at 100,000 xg through a 40% sucrose cushion. After resuspension in water, virus was stored at −70°.

Nucleocapsid protein was isolated by successive degradation of purified virus with EDTA and either $CaCl_2$ or LiCl, as follows. Outer capsid proteins were removed by incubating virus (3 mg/ml) in 50 mM EDTA - 0.01 M Tris-HCl pH 7.4 at 4° for 30 minutes. Subviral particles were recovered by ultracentrifugation (100,000 xg, 2-3 hrs, 4°) and resuspended in 0.01M Tris-HCl pH 7.4 or 0.01M sodium borate pH 9.0. They were then treated with either 1.5M $CaCl_2$ - 0.01M Tris-HCl pH 7.4 at 20° for 20-30 minutes or frozen in 2M LiCl - 0.01M sodium borate pH 9.0 at −70° for 4 days. Cores and undegraded particles were separated from solubilized protein by ultracentrifugation. EDTA and salts were removed by extensive dialysis at 4° against 0.01M Tris-HCl pH 7.4, unless otherwise indicated. The purity of the samples was examined by polyacrylamide electrophoresis (PAGE) Laemmli (1970) Nature 227:680-685.

B. Recombinant VP6

To produce the recombinant VP6, gene 6 of bovine rotavirus C486 was first cloned in the Pst1 site of pBR322. The resulting clone was digested with AhaIII and HpaIII and subcloned into the Sma I site of pAC373. After transfection into Escherichia coli, plasmids in recombinant ampicillin resistant colonies were screened by restriction enzyme analysis for inserts in the correct transcriptional orientation. To transfer gene 6 cDNA from the pAC373 vector to the Autographa californica nuclear polyhedrosis virus (AcNPV) DNA, Spodoptera frugiperda cells were cotransfected with wild-type AcNPV DNA using the calcium phosphate precipitation procedure as previously described. Smith et al. (1983) J. virol. 46:584-593. Following incubation at 27° C. for 4 hrs, the medium was removed and the cells observed with an inverted microscope for signs of infection. The extracellular virus was harvested at 5 days post-infection and plaqued on Spodoptera frugiperda cell monolayers. Recombinants were selected by identifying occlusion negative plaques with an inverted microscope. Positive plaques were further grown in microtiter dishes and nucleic acid dot blots on infected cells in these dishes were performed to verify the presence of gene 6. Plaque purification of positive supernatants from microtiter wells was performed and the virus from these plaques was used to propagate virus stocks.

To isolate VP6 from infected cells, the cells were first lysed with a buffer containing 1% NP40, 0.137M NaCl, 1 mM $CaCl_2$, 0.5 mM $MgCl_2$ and 0.1 mg/ml aprotinin. The lysate was then dialyzed in 0.01M citrate buffer pH 4.0 for 48 hrs during which time a precipitate which represented reassembled VP6 formed in the dialysis bag. The precipitate was then collected by centrifugation, then treated with 0.05M EDTA pH 5.0 for 1 hour and recentrifuged. The resulting .pellet contained purified VP6 reassembled spheres.

Rotavirus C486 is publicly available from the American Type Culture Collection (ATCC), 12301 Parklawn Dr., Rockville, Md. 20852, USA, where it was deposited under Accession No. VR-917 on Apr. 15, 1981. The pAC373 vector containing the rotavirus gene 6 cDNA was designated pAC373BRV6 and deposited with the ATCC on Aug. 31, 1987 under Accession No. 40362, where it will be maintained under the terms of the Budapest Treaty.

2. Binding Peptides

Seven different synthetic peptides were tested for the ability to bind VP6. The primary structure of the peptides was as follows:

| Peptide A | C—D—G—K—Y—F—A—Y—K—V—E—T—I—L—K—R—F—H—S—M—Y—G |
| Peptide B | C—N—I—A—P—A—S—I—V—S—R—N—I—V—Y—T—R—A—Q—P—N—Q—D—I—A |
| Peptide C | Y—Q—Q—T—D—E—A—N—K |
| Peptide D | D—E—A—N—K—K—L—G—P—R—E—N—V—A |
| Peptide E | R—N—C—K—K—L—G—P—R—E—N—V—A |
| Peptide F | R—N—C—K—K—L—G—P—R—M—M—R—I—N—W—K—K—W—W—Q—V |

-continued

| Peptide G | T—N—G—N—E—F—Q—T—G—G—I—G—N—L—P—I—R—N—W—N |

The various peptides were reacted for 30 minutes at 37° C. with 2.0 ug of purified VP6 from bovine rotavirus strain C486. Binding was then tested by gel electrophoresis. Two of these synthetic peptides (peptides A and B) bound to VP6 protein in the gel. A "laddering" effect was seen at locations corresponding to the 45K (molecular weight of VP6 monomer), 90K (molecular weight of VP6 dimer) and 135K (molecular weight of VP6 trimer) regions. Additional support for the binding of the two peptides to the various forms of VP6 was provided by the fact that the molecular weight increments in each ladder corresponded to the molecular weights of the synthetic peptide monomers. Definitive proof that the peptide bound to the VP6 protein was demonstrated by the fact that a ladder was detected at both the 45K and 90K regions with antisera produced against the synthetic peptides.

In order to further delineate the features of the binding peptide required for binding to VP6, several variant peptides derived from peptide B (also referred to as 84 TS) were synthesized and tested for their ability to bind to VP6. A list of the variant peptides along with their amino acid sequence and their binding ability is shown in Table 2, below.

acids 1-09 and 19-25 of peptide B were deleted and 3 amino acids including a cysteine were added to the amino terminal end, thereby decreasing the size of peptide B by 50%. Even though a cysteine residue is one of the requirements for peptide binding, its position appears to be somewhat important relative to that of the charged residues. For example, the peptide gp-41-SHT has a cysteine located in position 7 relative to the numbering system for peptide B, but its distance from the arginine residue is similar to that in peptide B and consequently binding to VP6 is observed.

In summary, the features important for peptide binding to VP6 relate to the spatial arrangement of a cysteine and arginine (or the charged amino acid) residues in the three-dimensional conformation of a peptide. Any peptide which has these features and consequently can bind to VP6 can be considered a binding peptide. An example of such a peptide is peptide A, which is derived from a sequence on the rotavirus VP3 protein, and is only related to peptide S in that it has a cysteine and arginine residue in the proper arrangement to allow binding to VP6.

3. VP6 Derived from Various Sources for Use as a Particle Carrier With or Without the Binding Peptide

TABLE 2

| NAME OF PEPTIDE VARIANTS | VARIANT PEPTIDES DERIVED FROM PEPTIDE B (84TS) | | | | | | BINDING TO VP |
|---|---|---|---|---|---|---|---|
| | AMINO ACID SEQUENCE[1] | | | | | | |
| | 1 | 5 | 10 | 15 | 20 | 25 | |
| 84 TS (PEPTIDE B) | C N I | A P A S I | V S R N I | V Y T R A | Q P N Q D I | A | + |
| 84 TS-CYS | * * * | * * * * * | * * * * * | * * * * * | * * * * * | * C | — |
| DISER | * * * | * * * * * | * S * * * | * * S * * | * * * * * | * | — |
| MONOSER | * * * | * * * * * | * * * * * | * * S * * | * * * * * | * | — |
| SHT | | | C G A * * | * * * * * | * * | | + |
| SR-SHT | | | C G A * S | * * * * * | * * | | |
| CP-41-SHT | D T F E G A P A C G A * | | | * * * * * | * * | | + |

[1] Amino acids are numbered 1-25 starting at the amino terminal end of Peptide B.
[2] The asterisks (*) indicate conserved amino acids from Peptide B.

The importance of the cysteine residue located on the binding peptide with respect to VP6 binding was apparent due to the fact that the reducing agent B-mercaptoethanol was able to abolish binding as discussed below in Example 4. However, the presence of a cysteine residue is not the only requirement for binding to VP6 as illustrated by the fact that the 84 TS-Cys peptide, which has the cysteine residue at its carboxy terminal instead of the amino terminal end, does not bind VP6. It was therefore hypothesized that the position of the cysteine relative to another charged residue, having the ability to interact electrostatically with charged residues on VP6, was also important. The other predominant charged residues on the parent peptide B are 2 arginines at positions 11 and 17. In order to test whether the arginine residues were indeed the important charged residues, 2 variant peptides were made. Specifically, the monoser variant peptide had arginine 17 replaced by an uncharged amino acid (serine) and the diser variant peptide had both arginine 11 and 17 replaced by serines. Since neither the monoser or diser bound to VP6, it appears that at least arginine 17 or both arginine 11 and 17 are required for binding to VP6.

The importance of the cysteine and arginines was further illustrated by the fact that a portion of peptide B (84 TS) could be deleted to produce the SHT peptide and still maintain binding to VP6. Specifically, amino Preliminary studies into the ability of VP6 to reassemble and to bind peptides in Example 2 were carried out using VP6 derived from bovine rotavirus strain C486. This virus strain belongs to subgroup I, and the epitope determining subgroup specificity is located on VP6. In order to determine whether VP6 derived from other sources will exhibit the same two properties (i.e., reassembly and binding peptides), SP6 derived from a subgroup II human rotavirus strain (strain WA) and a subgroup I VP6 produced by recombinant DNA technology (Example 1) were tested. The importance of testing a recombinant DNA product is that protein processing may not be the same as that in a natural infection, even though the genetic information is identical. If the processing is different, the resulting protein product may not have the intrinsic features necessary for reassembling or peptide binding. The recombinant DNA VP6 was produced as described in Example 1.

Figure 2B:
Figure 3:
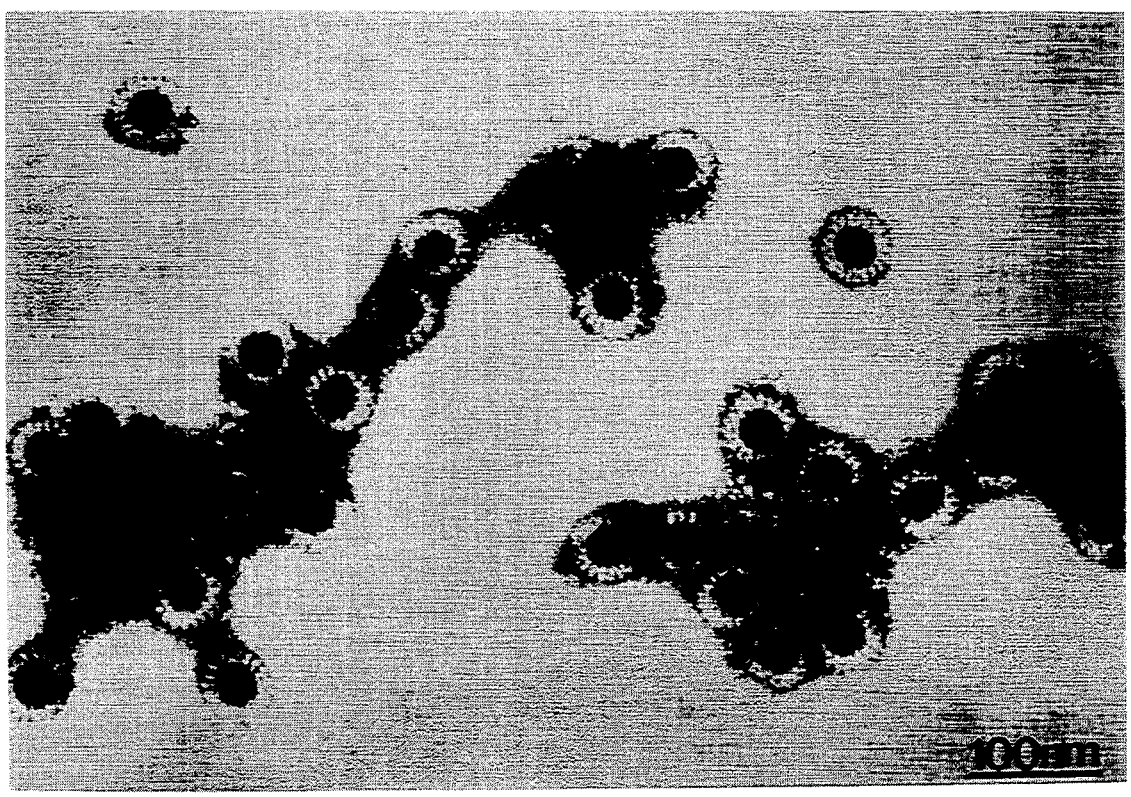
FIG. 3 is an electron micrograph of VP6 protein forming aggregated spherical particles in 0.01M citrate buffer pH 4.0 and dialyzed to pH 5.0.
Figure 4:
FIG. 4 is an electron micrograph of VP6 protein reassembled into various forms by dialyzing first to 0.01 M phosphate buffer, pH 6.0, and then to 0.01M citrate buffer, pH 4.0, at 4° C. The micrograph shows hexamers, small hexagonal lattices and tubes as well as sheets (arrows) consisting of a small-hole lattice. The arrow on the figure indicates the corresponding sheet on the original micrograph. Bars represent 100 nm.

The testing for the ability of VP6 to reassemble was carried out as follows. First, preparations containing no less than 0.1 ug of VP6/ul isolated from the subgroup II rotavirus or recombinant DNA-produced VP6 were dialyzed at 4° C. against 1 liter of 0.01M citrate buffer at pH 4.0 for 36 hours, with three changes of buffer during this time interval. Second, after dialysis, an aliquot of the preparation was examined by electron microscopy for the presence of particles. FIG. 2 illustrates that both subgroup II VP6 (Panel A) and recombinant DNA-derived VP6 (Panel B) can reassemble in spherical and tubular particles, indicating that they have the intrinsic features necessary for this type of process to occur.

The ability of the various VP6s to bind peptide was also tested. Preparations containing subgroup II rotavirus or recombinant DNA-produced VP6 were mixed with peptide B in a ratio of 1:10 (w/w). The mixture was then electrophoresed on a 10% polyacrylamide gel. Both subgroup II VP6 and recombinant DNA-derived VP6 were able to bind peptide as illustrated by a laddering in the region of the gel containing VP6.

Therefore, it appears that the features necessary for VP6 reassembly and peptide binding are present on both VP6 subgroups, various mammalian rotavirus VP6s, and recombinant VP6.

4. Characterization of VP6-Monomer-Binding Peptide Complex

Further characterization of the conditions required for binding of peptides in VP6 was carried out using peptide B.

Two micrograms of radiolabeled double-shelled rotavirus was reacted with 100 ug synthetic peptide B for min, 37° C. Prior to electrophoresis, the sample was aliquoted and treated with one of several buffers. The VP6-peptide B complex was treated with Laemmli buffer (0.0625M Tris-HCl pH 6.8, 4% sodium dodecyl sulfate, 8% glycerol and 0.05% bromphenol blue) for 30 min at 37° C. The same laddering effect described in Example 2 was observed. However, when B-mercaptoethanol was included in the sample buffer and the sample was boiled prior to electrophoresis, the ladders in both the 45K and 90K regions disappeared. This suggested that disulfide bridging was necessary to maintain the VP6-peptide B complex. However, the interaction between VP6 and peptide B could withstand such harsh treatments as boiling in sodium dodecyl sulfate. Identical results were obtained with subgroup II VP6, recombinant DNA-derived VP6 and the other binding peptides.

5. Characterization of VP6-Assembled Particles-Binding Peptide Complex

Binding of the peptide B to in vitro-assembled tubular and spherical particles composed of the VP6 monomers was also observed. These in vitro-assembled particles were produced by subjecting isolated VP6 to different pH conditions. Specifically, when isolated VP6 was placed in 0.01M citrate buffer pH 4.0 and dialyzed to pH 5.0, high aggregated, empty spherical particles occurred (FIG. 3). Tubular particles formed at pH 5.0 to 9.0 and aggregated at pH 5.0 (FIG. 4). VP6 was dialyzed first to 0.01M phosphate buffer (pH 5.0) and then to 0.01M citrate buffer (pH 4.0) at 4° C. The surface structure of the particles appears well ordered at pH 5.0 to 7.0 and less well ordered at pH 8.0 and 9.0. In addition to hexamers, small hexagonal lattices and tubes, the sample contained sheets (arrows) consisting of a small hole lattice. At the higher pH levels there was more amorphous material present than at pH 5.0 to 7.0, suggesting that perhaps less of the protein had polymerized. FIG. 5 summaries the relationship between VP6 monomers and VP6 oligomeric structures.

The spherical particles had a diameter of 62.0±15 nm (n=56) which is consistent with that of single-shelled virus particles. Tubes were 104±15 nm (n=58) in diameter. Immunoelectron microscopy and immunogold labeling were used to show that the tubes consisted of the VP6 protein. Specifically tubes were labeled with immunogold when monoclonal antibody specific for VP6 was used as the primary antibody, but were not labeled when normal mouse serum was used as the primary antibody.

To confirm that the synthetic peptides could bind to these in vitro-assembled particles, grids were coated with antiserum to VP6, or with antiserum against peptide B. The number of tubular particles trapped on equivalent areas of the two types of grid was then counted. When tubular particles were not reacted with peptide B, grids coated with antibodies to VP6 trapped over 30 times as many tubes as did grids coated with antibodies against peptide B. However, when tubular particles were first reacted with peptide B, then the number of tubular particles trapped on grids coated with antibodies against the peptide B was at least 5 times as large as for unreacted tubular particles (Table 3).

TABLE 3

IMMMUNOSORBENT SERUM ELECTRON MICROSOPY OF VP6 TUBES WITH AND WITHOUT PEPTIDE B

| Antibody Used to Coat Grid | Sample | Number of Tubes/ Counted Area |
|---|---|---|
| Antiserum to VP6 | Tubes | 300 |
| Antiserum to Peptide B | Tubes | 10 |
| Antiserum to Peptide B | Tubes with Peptide B | 53 |

The binding of the peptide B to in vitro-assembled spherical and tubular structures was further confirmed by the observation of a ladder formation of the VP6 protein derived from these particles on a polyacrylamide gel.

The specific nature of this binding phenomenon was investigated further by examining the primary amino acid sequence of the peptide binding site, and the number of VP6 binding sites. The conditions for binding to occur have already been described above.

The number of potential binding sites on VP6 can be estimated by counting the number of rungs on a VP6 ladder formation. There is a shift from one rung to four rungs as the ratio of peptide to VP6 increases from 2:1 to 25:1. This indicates that there may be as many as four VP6 binding sites. However, since the synthetic peptide forms dimers of itself in solution, it is not possible to determine, via this type of experiment, whether there are four primary VP6 binding sites or two primary VP6 binding site, with bound peptide dimers to each VP6 binding site.

6. Immunogenicity of the Various Forms of VP6

The immunogenicity of the VP6 monomer and of tubular and spherical forms of VP6 assembled into particles (FIG. 4) were investigated. As illustrated in Table 4 below, both particle types were very immunogenic based on a comparison of antibody titers produced after immunizing mice with 10 ug of either the VP6 monomer, spherical particles, tubular particles or naturally occurring incomplete virus particles. The immunogen was administered three times over an eight-week period and was emulsified in Freund's Incomplete Adjuvant.

TABLE 4

Immunogenicity of Various Forms of VP6 Monomeric and Oligomeric Structures as Compared to Incomplete Rotavirus Particles

| Form of VP6 Used for Immunization of Mice | Antibody Titer Determined by Enzyme-linked Immunosorbent Assay Using the Incomplete Virus Particle as the Capture Antigen |
| --- | --- |
| VP6 Monomer | $10^{4.5}$ |
| Tubular Structure | $10^{6.5}$ |
| Spherical Structure | $10^{7.9}$ |
| Incomplete Virus | $10^{7.0}$ | cl 7. Examples of Immunizing with VP6 Assembled Particles -Epitope Constructs

This Example demonstrates the efficacy of the VP6-assembled particles as an immunological carrier for epitopes whose amino acid sequences were derived from parasitic, bacterial and viral immunogens. These represent protein and glycoprotein haptens as well as a bacterial carbohydrate moiety which demonstrates the utility of the carrier with haptens other than those of protein origin.

A. Production of VP6-Assembled Particles (spherical carrier)

Bovine rotavirus (strain C486 rotavirus subgroup I was grown in MA-104 cells (monkey kidney), harvested, then purified and concentrated by ultracentrifugation. The VP6 was extracted from purified virus preparations by successive treatment with ethylene-diamine tetra acetic acid (EDTA) and lithium chloride ($LiCl_2$). Preparations containing VP6 were then dialyzed to pH 4.0 at which time a precipitate formed, representing aggregated spherical particles, as described above. The aggregated spheres were dispersed by dialysis to pH 5.0 or higher and then were stored at −70° C.

Verification of the composition of the particles was by gel electrophoresis and immunoblot ELISA, using antisera specific for VP6. Verification of the ultrastructure of the particles was by electron microscopy.

B. Synthesis of SHT Peptide-Epitope (Hapten) Constructs

SHT peptide-epitope (hapten) constructs were synthesized using Merrifield's solid-phase methodology on an Applied Biosystems 430A peptide synthesizer.

The peptide named 84 TS (MW 2,734) is identical to binding Peptide B described above in Table 2. The amino acid sequence for this peptide was derived from the trypsin cleavage site of bovine rotavirus VP3 spanning amino acids 231–254 and is as follows: H-Cys-Asn-Ile-Ala-Pro-Ala-Ser-Ile-Val-Ser-Arg-Asn-Ile-Val-Tyr-Thr-Arg-Ala-Gln-Pro-Asn-Gln-Asp-Ile-Ala-OH. The cysteine at position 1 was added to facilitate coupling to a carrier protein and is not present in the natural sequence. Reevaluation of the criteria required for binding of Peptide B to VP6-assembled particles enabled the generation of a shortened version of the binding peptide which is referred to as SHT (Table 2). The SHT peptide is composed of amino acids 1 and 10–18 from binding Peptide B, plus 2 amino acids to achieve proper spacing. The amino acid sequence of SHT is as follows: H-Cys-Gly-Ala-Ser-Arg-Asn-Ile-Val-Tyr-Thr-Arg-Ala-OH. The amino acids glycine (Gly) and alanine (Ala) at positions 2 and 3, respectively, are spacers to distance the cysteine (Cys) from the arginine (Arg).

The remaining three-peptide constructs are composed as follows. Amino acids 1 and 10–18 from Peptide B plus the two spacer amino acids (i.e., SHT) comprise the first 12 amino-terminal amino acids of the construct and the following three amino acid (either Ala-Pro-Ala or Gly-Ala-Pro) are spacers which distance the SHT portion of the construct from a specific epitope that comprises the remaining portion of the peptide construct. The peptide designated pili-SHT (MW 3,174) has its amino terminal end comprised of the SHT peptide and its carboxy terminal sequence from the amino terminal region of the F pilin of E. coli. The amino acid sequence of the entire construct is: H-Cys-Gly-Ala-Ser-Arg-Asn-Ile-Val-Tyr-Thr-Arg-Ala-Ala-Pro-Ala-Gly-Ala-G ly-Ser-Ser-Gly-Gln-Asp-Leu-Met-Ala-Ser-Gly-Asn-Thr-Thr-Val-A la-OH. The underlined portion indicates the epitope whose sequence was derived from the F pilin of E. coli, and to which the immune response is to be directed.

The peptide designated Leishmania-SHT (MW 3,876) is comprised of the SHT peptide at the amino terminal end and its carboxy terminal end is derived from a sequence of glycoprotein 63 of the Leishmania donovani. The amino acid sequence of the construct is: H-Cys-Gly-Ala-Ser-Arg-Asn-Ile-Val-Tyr-Thr-Arg-Ala-Ala-Pro-Ala-Val-Asn-Trp-Gly-Ala-Leu Arg-Ile-Ala-Val-Ser-Thr-Glu-Asp-Leu-Lys-Thr-Pro-Ala-Tyr-Ala-OH. Again, the underlining indicates the epitope whose sequence was derived from glycoprotein 63 of Leishmania donovani and to which the immune response is to be directed.

The peptide designated BHV-1-SHT (MW 4,645) is comprised of the SHT peptide at the amino terminal, while its carboxy terminal is derived from an epitope which spans amino acids 323–345 of bovine herpes virus-1 glycoprotein gl (or gB). Hence, the amino acid sequence of the construct is: H-Cys-Gly-Ala-Ser-,Arg-Asn-Ile-Val-Tyr-Thr-Arg-Ala-Gly-Ala-Pro-Glu-His-Thr-Ser-Tyr-Ser-Pro-Glu-Arg-Phe-Gln-Gln-Ile-Glu-Gl y-Tyr-Tyr-Lys-Arg-Asn-Met-Ala-Thr-Ala-Ala-OH. The two carboxy terminal alanines are spacers. The underlining again indicates the epitope whose sequence was derived from AA323–345 of BHV-1 glycoprotein and to which the immune response is to be directed. In order to evaluate the level of the immune response induced by this epitope, a larger sequence spanning amino acids 319–352 on bovine herpes virus 1 glycoprotein gI (or gB) was used as the capture antigen in ELISAs, described below. The amino acid sequence of this larger peptide, called BHV-1, is: Gly-Ala-His-Arg-Glu-His-Thr-Ser-Tyr-Ser-Pro-Glu-Arg-Phe-Gln-Gln-Ile-Glu-Gly-Tyr-Tyr-Lys-Arg-Asp-Met-A la-Thr-Gly-Arg-Arg-Leu-Lys-Glu-Pro-Ala-Glu. The terminal 2 amino acids alanine (Ala) and glutamic acid (Glu) are spacers.

A slightly different approach was used in order to produce a SHT peptide-epitope construct where the epitope was a carbohydrate moiety. A new SHT peptide was prepared having the sequence shown in Table 2, but with the following peptide spacer at the carboxy terminal instead of the tripeptide described above: -Ala-Pro-Ala-Lys-Ala-Lys-Ala-Lys-Ala-OH. This SHT version has MW 2,054. A capsular polysaccharide moiety was isolated from the bacterium Haemophilus pleuropneumoniae, and then oxidized, hydrolyzed and reductively aminated to the SHT peptide. See Altman et al. (1986) Biochem & Cell Biol. 64:707–716; Porter et al. (1986) J. Immunol. 137:1181–1186. This provided a carbohydrate-SHT (CHO-SHT) construct. (NOTE: The taxonomists have recommended that the species name Haemmophilus be replaced with the name Actinobacillus.)

C. Formation of VP6 Assembled Particle - Epitope Constructs

In order to generate VP6 assembled particle-peptide complexes containing the SHT peptide and an epitope of protein origin, the VP6 assembled particles and the peptide constructs were mixed together in a ratio of 1:10 (w/w), respectively, since this ratio produced a complete ladder indicating that most of the potential binding sites on VP6 were occupied by the peptide. However, any ratio from 1:1 up to 1:10 would produce laddering of VP6, albeit to different extents. Verification of binding of the peptide construct to VP6 and establishment of the ratio of VP6 assembled particle to peptide construct to be used in preparations for in vivo studies, was by electrophoresis of the preparations on polyacrylamide gels and observation of VP6 laddering, a phenomenon described previously. Verification of the immunoreactivity of the peptide haptens was immunoblot-ELISA reactions using antisera specific for the protein from which the hapten (epitope) was derived.

In order to generate a VP6 assembled particle-peptide complex where the epitope was a carbohydrate, the VP6 assembled particles and CHO-SHT binding to VP6 was by polyacrylamide gel electrophoresis. In this case, high molecular weight material was observed which represented the VP6-CHO-SHT complex. Verification of the compositions of the high molecular weight complex, observed in a polyacrylamide gel, was by an immunoblot-ELISA reaction using antisera specific for the carbohydrate and antisera specific for the SHT peptide.

D. Immunization and Serological Responses

In general, for immunization trials 1 to 4, groups of 5 to 10 CD-1 mice were inoculated with one of the four VP6 assembled particle-peptide complexes described above according to the experimental designs shown in Tables 5, 6, 7 and 8. The VP6 assembled particle to peptide construct ratio was always 1:10 (w/w), respectively. The mice used in these experiments were rotavirus-free unless otherwise stated.

The basic immunization schedule was the same for all trials, except number 5. Basically, animals were bled at week 0 and then immunized intramuscularly with 100 ul of the test preparation at week 1 and then again at week 4. In some trials, a third immunization was administered. The type of immunogen and purpose for immunization in each trial is outlined below. Pooled serum samples were obtained from each group of mice on a weekly interval. Assessment of antibody levels specific for the VP6 assembled particles (spheres) or the peptide constructs (hapten) was by ELISA and is appropriately indicated in FIGS. 6–8 corresponding to Trials 2 through 4, respectively, while the immunization protocols were shown in Tables 5 through 8, corresponding to Trials 1 through 4, respectively.

Trial 1 (Table 5)

The objective of this trial was to evaluate the dose response to the spherical carrier—84TS complex using either Freund's adjuvant or dimethedioctodecyl ammonium bromide (DDA) adjuvant, and to investigate the possibility of carrier suppression (described below). The immunogen used for primary and secondary immunization was the spherical carrier-84TS complex. The immunogen used for tertiary immunization to investigate carrier suppression was the spherical carrier—272-295 SHT complex.

Table 5 outlines the experimental design used to investigate the dose response to the VP6 assembled particle-84 TS peptide complex using either Freund's adjuvant or dimethyldioctodecyl ammonium bromide (DDA) adjuvant. This study also attempts to investigate the possibility of a carrier suppression phenomenon which is a recently recognized immunoregulatory mechanism and has been described in the literature for other carriers currently in use. Basically, carrier suppression occurs when a host is immunized with a hapten conjugated to an immunogenic carrier to which the animal has been previously exposed or immunized. A strong secondary response is produced to the carrier, but the host fails to produce antibodies to the linked hapten. In this experiment, therefore, animals which were immunized twice with the VP6 assembled particle-84TS peptide complex were then reimmunized a third time, at week 19, with the VP6 assembled particle—275-295—SHT peptide complex. The 275-295 peptide sequence was derived from a neutralizing domain on bovine rotavirus VP7 and represents another example of a viral peptide attached to VP6 assembled particles. The VP7 sequence is: Pro-Thr-Thr-Ala-Pro-Gln-Thr-Glu-Arg-Met-Met-Arg-Ile-Asn-Trp-Lys-Lys-Trp-Trp-Gln-Val.

The results illustrated that the VP6 assembled particles are effective in inducing high levels of antibody in vivo in both themselves (approximately 6.0–6.5 $\log_{10}$) as well as to the peptide attached to them (approximately 5.5–6.0 $\log_{10}$) when a dose equivalent to 1 ug of VP6 assembled particles is administered. In fact, the level of antibody specific for the peptide at this dose was almost identical to a dose equivalent to 10 ug of peptide bound to 1 ug of VP6 assembled particles and only slightly less than that using 100 ug peptide bound to 10 ug of VP6 assembled particles. Furthermore, the level of antibody produced to the peptide was significantly higher than that induced by the equivalent amount of unbound or "free" peptide, except at the 100 ug dose of "free" peptide, where an anti-peptide response of 5.5 $\log_{10}$ was observed.

A comparison of antibody levels in sera from animals administered preparations containing either PCA or DDA illustrated that these two adjuvants were equally effective, at least at the two doses investigated. In addition, no carrier suppression was observed since an antibody response (approximately 4.5 $\log_{10}$) to peptide 275–295-SHT could be detected at week 20, when the VP6 assembled particle—275-295—SHT peptide complex was administered at week 19.

TABLE 5

EXPERIMENTAL DESIGN FOR TRIAL I - DOSE RESPONSE TO SPHERICAL CARRIER +/− PEPTIDES + DDA OR FCA ADJUVANTS

| # Mice/ Group | Immunization at Weeks 1 and 4 ug Carrier-ug peptide 84TS[a] | Immunization at Week 19 ug Carrier-ug Peptide 275-295-SHT[b] | Adjuvant[c] |
|---|---|---|---|
| 5  | 0.1-0       | 0-0      | FCA/FIA |
| 5  | 1.0-0       | 0-0      | FCA/FIA |
| 5  | 10-0        | 0-0      | FCA/FIA |
| 10 | 0.1-1.0     | 0.1-1.0  | FCA/FIA |
| 10 | 1.0-10      | 1.0-10   | FCA/FIA |
| 10 | 10-100      | 10-100   | FCA/FIA |
| 5  | 1.0-0       | 0-0      | DDA |
| 5  | 10-0        | 0-0      | DDA |
| 5  | 1.0-10      | 1.0-10   | DDA |
| 10 | 10-100      | 10-100   | DDA |
| 10 | 0-0         | 0-0      | FCA/FIA |
| 5  | 1.0 virus 0 | 0-0      | FCA/FIA |
| 5  | 0-0         | 0-0      | FCA/FIA |
| 5  | 0-0         | 0-0      | DDA |
| 5  | 0-1.0       | 0-0      | FCA/FIA |
| 5  | 0-10        | 0-0      | FCA/FIA |
| 5  | 0-100       | 0-0      | FCA/FIA |

[a]The ratio of spherical carrier to peptide construct is 1:10.
[b]Peptide 275-295 was derived from VP7 of bovine rotavirus and was linked to the carrier via the SHT peptide. The carrier - 275-295-SHT complex was administered at week 19 in order to investigate carrier suppression phenomenon.
[c]Freund's Complete Adjuvant (FCA) was used for the primary immunization and Freund's incomplete Adjuvant (FIA) was used for the secondary immunization.
DDA - dimethyl dioctodecylammonium bromide is a quaternary amino surfactant which acts as an adjuvant. It was used for both primary and secondary immuniztion where specified.

Figure 6:
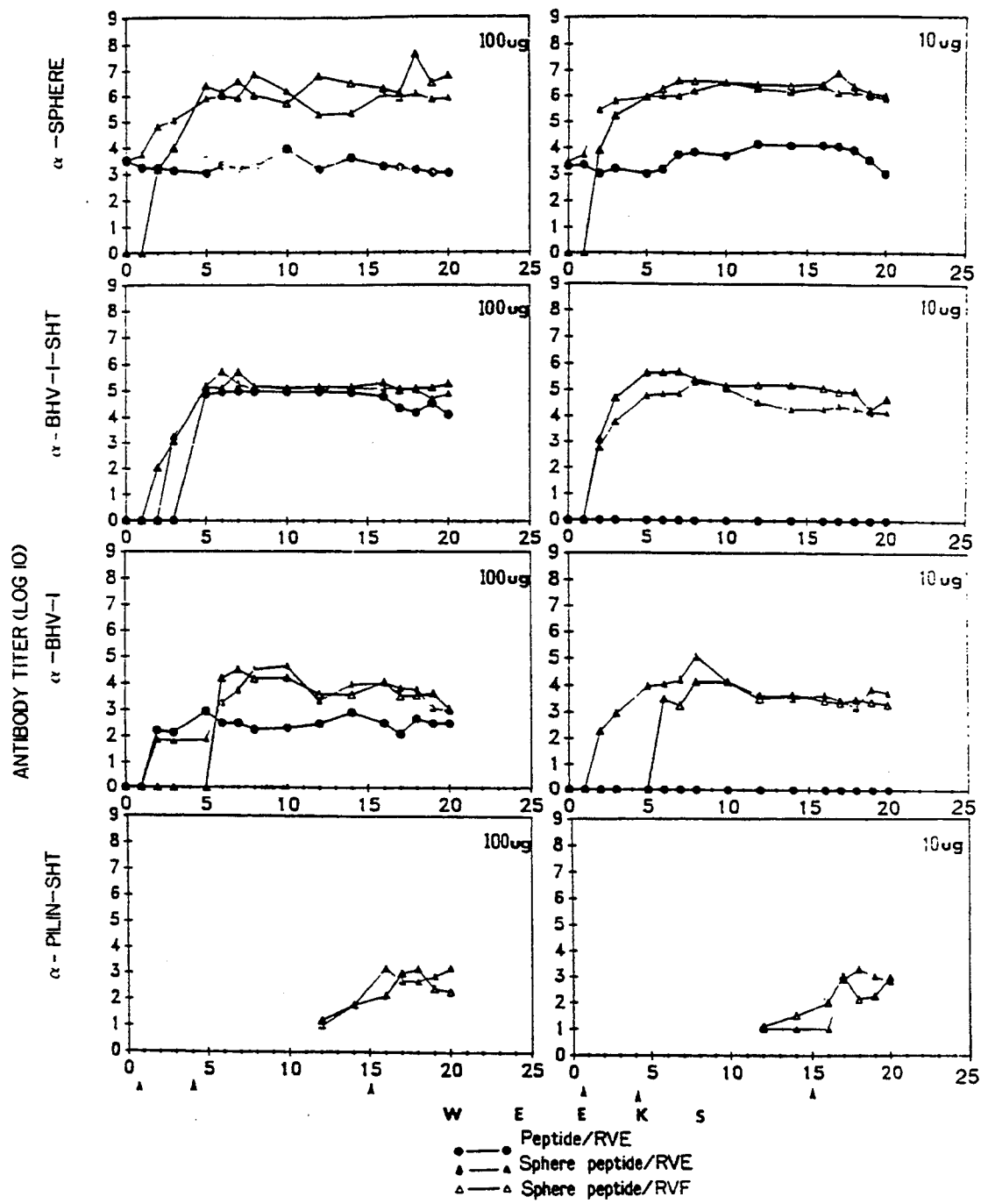
FIG. 6 depicts dose-response curves to spherical VP6 carrier protein with and without various epitope-bearing molecules complexed therewith.

Trial 2 (Table 6 FIG. 6)

The objective of this trial was to evaluate the dose response to spherical carrier-BHV-1-SHT complex in rotavirus-free and rotavirus-exposed mice, and to investigate the possibility of carrier suppression. The immunogen used for primary and secondary immunization was the spherical carrier-BHV-1-SHT complex. The immunogen used for tertiary immunization to investigate carrier suppression was the spherical carrier-pilin-SHT complex.

Table 6 outlines the experimental design used to investigate the dose response to the VP6 assembled particle-BHV-1-SHT complex in both rotavirus-free and rotavirus-exposed mice. In a natural situation some animals as well as humans have a preexisting antibody titer to rotavirus. Therefore, it was important to investigate whether the presence of such antibodies would influence the immune response to the VP6 assembled particle-peptide complex.

FIG. 6 illustrates the antibody responses to the VP6 assembled particle (anti-sphere), the BHV-1-SHT peptide (anti-BHV-1-SHT), and to pilin-SHT (anti-pilin-SHT). The latter antibody response was used to investigate the possibility of carrier suppression. The quantity of peptide in the VP6-assembled BHV-1-SHT peptide preparation administered to mice is indicated on the top right corner of each panel. The arrows below the axis indicating weeks denote the time of immunization.

TABLE 6

EXPERIMENTAL DESIGN FOR TRIAL 2 - DOSE RESPONSE TO SPHERICAL CARRIER + PEPTIDES IN ROTAVIRUS-FREE (RVF) AND ROTAVIRUS-EXPOSED (RVE) MICE

| # Mice/ Group | Rotavirus Status of Mice[a] | Immunization at Weeks 1 and 4 ug Carrier-ug peptide BHV-1-SHT[b] | Immunization at Week 19 ug Carrier-ug Peptide pili-SHT[b,c] | Adjuvant[c] |
|---|---|---|---|---|
| 10 | RVF | 10-100 | 10-100 | FCA/FIA |
| 10 | RVE | 10-100 | 10-0   | FCA/FIA |
| 10 | RVF | 1-10   | 1-100  | FCA/FIA |
| 10 | RVE | 1-10   | 1-10   | FCA/FIA |
| 10 | RVE | 0-100  | 0-0    | FCA/FIA |
| 10 | RVE | 0-10   | 0-0    | FCA/FIA |
| 10 | RVF | 0-0    | 0-0    | FCA/FIA |
| 10 | RVE | 0-0    | 0-0    | FCA/FIA |

[a]Rotavirus-free (RVF) and rotavirus-exposed (RVE) mice.
[b]The ratio of carrier to peptide construct is 1:10.
[c]The carrier - pili-SHT complex was administered at week 15 in order to investigate the phenomenon of carrier expression.
[d]Freund's Complete Adjuvant (FCA) was used for the primary immunization and Freund's Incomplete Adjuvant (FIA) was used for the secondary immunization.

FIG. 6 illustrates that there was no significant difference between the level of antibody produced in rotavirus-free (RVF) and rotavirus-exposed (RVE) mice to the VP6 assembled particles and the BHV-1-SHT peptide, even though the RVE mice had an anti-sphere titer of approximately 3 logs at the start of the immunization schedule. The lowest dose tested in this experiment consisted of 10 ug of BHV-1-SHT peptide and 1 ug of VP6 assembled particles. As illustrated in FIG. 6, 10 ug of the BHV-1-SHT peptide alone did not induce a detectable antibody response to the peptide, whereas the same quantity of peptide bound to the VP6 assembled particles induced an antibody response of approximately 5 logs.

Since the carboxy terminal sequence of the BHV-1-SHT peptide was derived from a larger (BHV-1) peptide described above, it was of interest to test the reactivity of the antibodies specific for the BHV-1-SHT peptide with the parent BHV-1 peptide alone. The level of antibody reacting with the BHV-1 peptide gave an indication of the immunogenicity of the carboxy terminal portion of the BHV-1-SHT peptide; the portion containing the epitope to which an immune response was desired. As illustrated in the anti-BHV-1 panels of FIG. 6, there was a significant antibody response produced against the carboxy terminal portion of the peptide construct; i.e., the BHV-1 peptide.

The carrier suppression phenomenon was also investigated in this experiment using a different VP6 assembled particle peptide combination than that described in Trial 1. After two immunizations with the VP6 assembled particle-BHV-SHT peptide complex, the VP6 assembled particle-pilin-SHT peptide complex was administered at week 15. As illustrated in FIG. 6, previously existing antibodies to the VP6 assembled particle did not affect the production of antibodies to a new peptide (i.e., pilin-SHT) presented on VP6 assembled particles. Furthermore, carrier suppression was not observed in either RVF or RVE mice since antibodies specific for the pilin-SHT peptide were detected (anti-pilin-SHT panel, FIG. 6). Antibodies detected to the pilin-SHT prior to immunization at week 15 were due to reaction with the shared amino terminal portion of the peptide constructs (i.e., SHT peptide).

Figure 7:
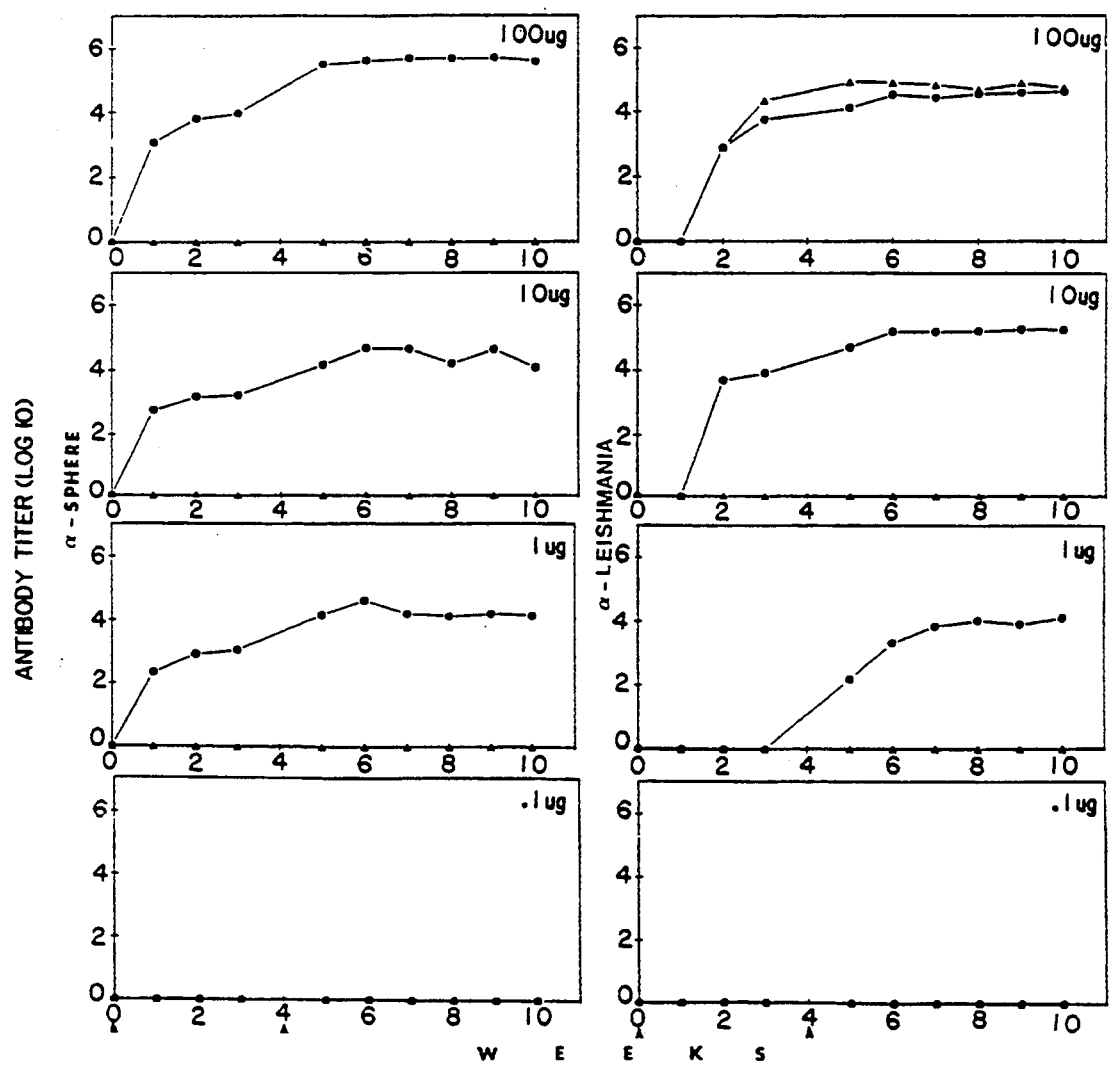
FIG. 7 depicts dose-response curves to spherical VP6 carriers complexed with or without various epitope-bearing molecules.
Figure 8:
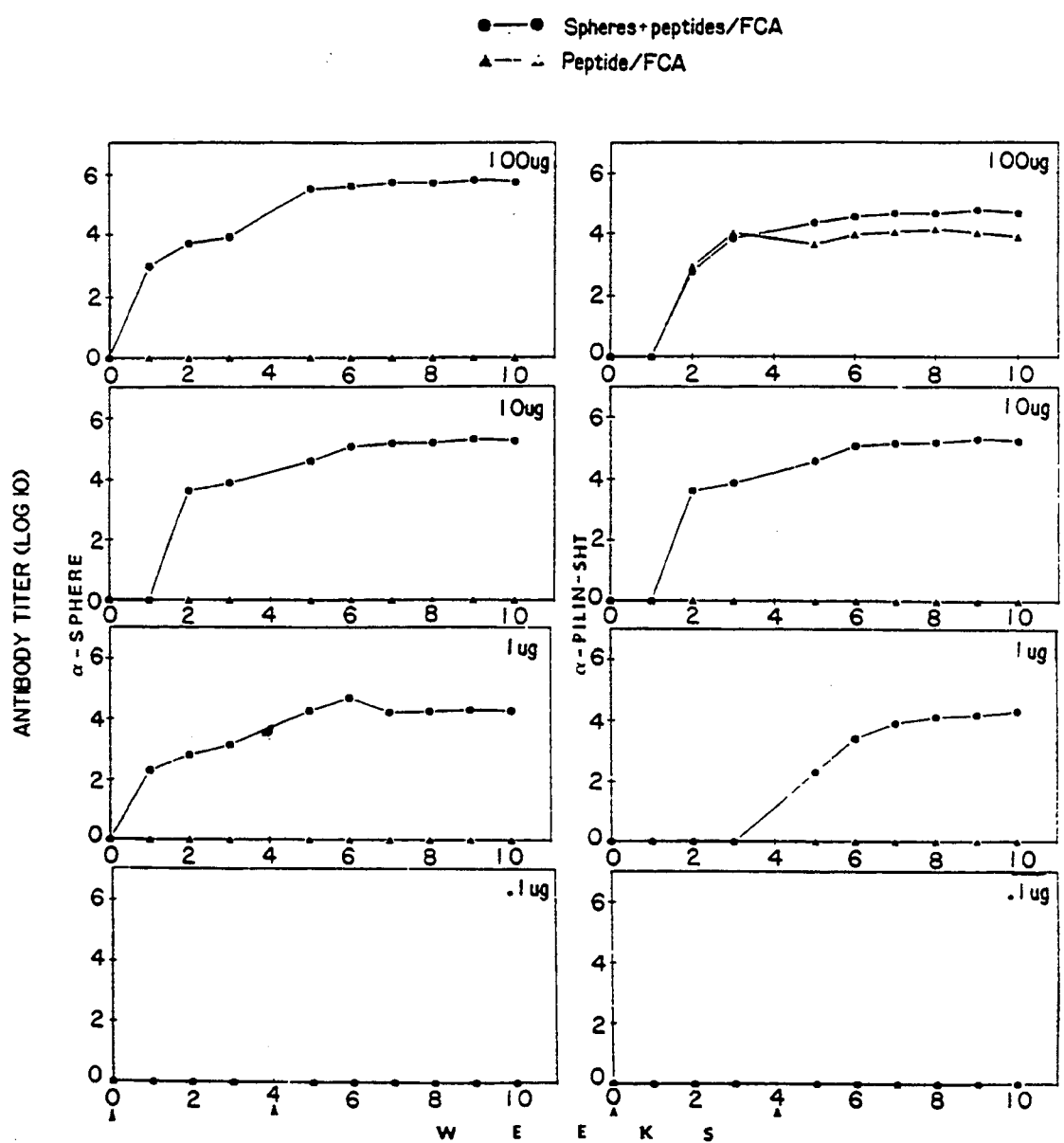
FIG. 8 depicts dose-response curves to spherical VP6 carrier protein with or without epitope-bearing molecules complexed therewith.

Trial 3 (Table 7 and FIG. 7) and Trial 4 (Table 8 and FIG. 8)

The objectives of these trials were to evaluate the dose response to spherical carrier-Leishmania-SHT (Trial 3) and spherical carrier-pilin-SHT (Trial 4). The immunogens used for primary and secondary immunization were spherical carrier-Leishmania-SHT or spherical carrier-pilin-SHT complexes.

Tables 7 and 8 outline the experimental design to investigate the dose response to the VP6 assembled particle-leishmania-SHT peptide complex and to the VP6 assembled particle-pilin-SHT peptide complex, respectively. The antibody response to the VP6 assembled particles and to both the peptide constructs, shown in FIGS. 7 and 8, illustrate that the lower quantity of immunogen which elicits an antibody response in mice after two immunizations is 0.1 ug of VP6 assembled particles bound to 1.0 ug of peptide. In contrast, for both the Leishmania-SHT (FIG. 7) and pilin-SHT peptides (FIG. 8), only 100 ug of free peptide was able to elicit an immune response.

TABLE 7

EXPERIMENTAL DESIGN FOR TRIAL 3: DOSE RESPONSE TO SPHERICAL CARRIER + LEISHMANIA-SHT PEPTIDE

| # Mice/Group | ug Carrier–ug Peptide Leishmania-SHT[a] | Adjuvant[b] |
|---|---|---|
| 10 | 10–100 | FCA/FIA |
| 10 | 1.0–10 | FCA/FIA |
| 10 | 0.1–1.0 | FCA/FIA |
| 10 | 0.01–0.1 | FCA/FIA |
| 10 | 0–100 | FCA/FIA |
| 10 | 0–10 | FCA/FIA |
| 10 | 0–1.0 | FCA/FIA |
| 10 | 0–0.1 | FCA/FIA |
| 10 | 0–0 | FCA/FIA |
| 10 | 1.0 rotavirus 0 | FCA/FIA |

[a]The ratio of spherical carrier to peptide construct is 1:10.
[b]Freund's Complete Adjuvant (FCA) was used for primary immunization and Freund's Incomplete Adjuvant (FIA) was used for secondary immunization.

TABLE 8

EXPERIMENTAL DESIGN FOR TRIAL 3: DOSE RESPONSE TO SPHERICAL CARRIER + PILIN-SHT PEPTIDE

| # Mice/Group | ug Carrier–ug Peptide Pilin-SHT[a] | Adjuvant[b] |
|---|---|---|
| 10 | 10–100 | FCA/FIA |
| 10 | 1.0–10 | FCA/FIA |
| 10 | 0.1–1.0 | FCA/FIA |
| 10 | 0.01–0.1 | FCA/FIA |
| 10 | 0–100 | FCA/FIA |
| 10 | 0–10 | FCA/FIA |
| 10 | 0–1.0 | FCA/FIA |
| 10 | 0–0.1 | FCA/FIA |
| 10 | 0–0 | FCA/FIA |
| 10 | 1.0 rotavirus 0 | FCA/FIA |

[a]The ratio of spherical carrier to peptide construct is 1:10.
[b]Freund's Complete Adjuvant (FCA) was used for primary immunization and Freund's Incomplete Adjuvant (FIA) was used for secondary immunization.

Figure 9:
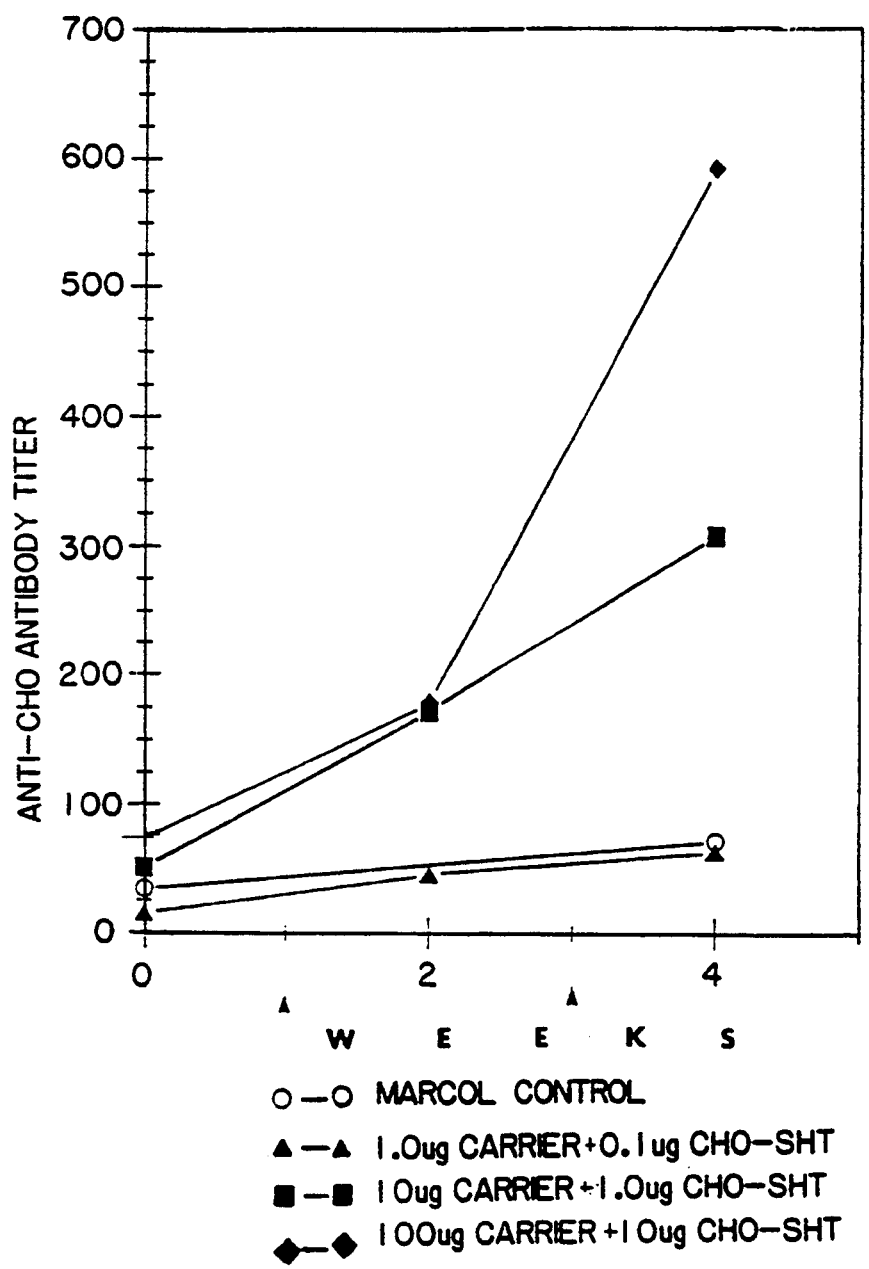
FIG. 9 depicts a dose-response curve for a spherical VP6 carrier protein complexed with an epitope-bearing molecule.

Trial 5 (Table 9 and FIG. 9)

The objective of this trial was to evaluate in swine the dose response to spherical carrier-CHO-SHT complex. The immunogen used for primary and secondary immunization was the spherical carrier-CHO-SHT complex.

In order to test the VP6 assembled particle-CHO-SHT complex, 16 pigs were randomized into 4 groups of 4 pigs each. One group of pigs was left as unvaccinated controls. The other three groups were immunized with different doses of this preparation as shown in Table 9 and according to the following immunization schedule.

TABLE 9

EXPERIMENTAL DESIGN FOR TRIAL 5: MEASURING SWINE ANTIBODIES TO SPHERICAL CARRIER + CARBOHYDRATE-PEPTIDE (CHO-SHT

| # Pigs/Group | ug Carrier–ug CHO-SHT[a] | Adjuvant[b] |
|---|---|---|
| 4 | 1.0–0.1 | marcol 52 |
| 4 | 10–1.0 | marcol 52 |
| 4 | 100–10 | marcol 52 |
| 4 | 0–0 | marcol 52 |

[a]The ratio of carrier to CHO-SHT is 10:1.
[b]Marcol 52 - an oil-based.

Immunization Schedule

| Weeks | Procedure |
|---|---|
| 0 | randomize 16 pigs into 4 groups and bleed |
| 1 | vaccinate intramuscularly, left neck, 2 ml dose |
| 3 | bleed, boost intramuscularly, right neck, 2 ml dose |
| 4 | bleed |
| 5 | bleed |

The antibody responses to the carbohydrate moiety were determined by ELISA and are shown in FIG. 9. Both 1.0 ug of CHO-SHT bound to 10 ug of VP6 assembled particles (carrier) and 10 ug of CHO-SHT bound to 100 ug of VP6 assembled particles induce an immune response which was significantly higher than that detected in animals given marcol 52 adjuvant alone or 0.1 ug of CHO-SHT bound to 1.0 ug of VP6 assembled particles.

8. Covalent Coupling of Haptens to VP6

The peptide designated FMDV-SHT is comprised of the SHT peptide at the amino terminal end. The amino acid sequence of the construct is: H-Cys-Gly-Ala-Ser-Arg-Asn-Ile-Val-Tyr-Thr-Arg-Ala-Gly-Ala-Gly-Val-Pro-Asn-Leu-Arg-Gly-Asp-Leu-Gln-Val-Leu-Ala-Gln-Lys-Val-Ala-Arg-Thr-Ala-Ala-O H. The underlining indicates the epitope whose sequence was derived from a sequence from protein VP1 the $O_1$ Kaufbeuren strain of foot and mouth disease ($O_1$ K FMDV).

The FMDV portion of the above peptide plus the l C terminal spacer, that is H-Val-Pro-Asn-Leu-Arg-Gly-Asp-Leu-Gln-Val-Leu-Ala-Gln-Lys-Val-Ala-Arg-Thr-Ala-Ala-OH, was also synthesized, this underlining indicates the spacer. This peptide without the SHT sequence (FMDV) was then chemically coupled using 1-ethyl-3-(3-dimethyl aminopropyl)-carbodiimide HCl in carbonate buffer pH 9.0 to VP6 spheres reassembled (described previously) for 4–8 hrs. The VP6 spheres with the peptide bonded to them were isolated from the reaction mixture by ultracentrifugation on a cesium chloride gradient. The product was recovered at a density approximately equal to that of the reassembled spheres.

This preparation was then used to immunize groups of mice. When used with Freund's Complete Adjuvant, the groups which were given 10 or 100 ug per mouse responded with anticarrier antibodies and the mice given 100 ug/mouse responded with antipeptide to a titer of $1/10^3$. This shows peptides or other molecules can be covalently attached through one of several possible activating reactions to VP6 spheres without the use of a binding peptide. This alternate method of attachment to the VP6 spheres does not interfere with the production of antibodies to these haptenic molecules.

The foregoing examples provide specific embodiments of the present invention, other embodiments being readily within the skill of the art. Thus, the scope of the present invention is defined by the following claims without limitation to the foregoing examples.

We claim:

1. An immunological carrier complex that raises an immunological response in a mammal to an epitope, said complex comprising:
   a molecule containing an epitope-bearing moiety, coupled to a carrier protein comprising the amino acid sequence of a rotavirus VP6 inner capsid protein.

2. The complex of claim 1 wherein said epitope-bearing moiety is a lipid.

3. The complex of claim 2 wherein said lipid is selected from the group consisting of a glycolipid, a fatty acid, a glycerol derivative, a prostaglandin, and a lipopeptide.

4. The complex of claim 1 wherein said epitope-bearing moiety is a nucleic acid.

5. The complex of claim 1 wherein said carrier protein is in the form of a particle.

6. The complex of claim 5 wherein said particle is a spherical particle.

7. The complex of claim 5 wherein said particle is a tubular particle.

8. The complex of claim 1 wherein said coupling of said carrier protein and said molecule is through conventional chemical coupling.

9. The complex of claim 1 wherein said coupling of said carrier protein and said molecule is through protein-protein interaction.

10. The complex of claim 9 wherein said protein-protein interaction is between said carrier protein and a peptide portion of said molecule capable of binding to said carrier protein, said peptide portion having an amino acid sequence which generates a spatial arrangement of a cysteine and arginine residues in the three-dimensional conformation of said peptide portion which provides capability to bind said carrier protein.

11. The complex of claim 9 wherein said protein-protein interaction is between said carrier protein and a peptide portion of said molecule comprising an amino acid sequence selected from the group consisting of:
   (a) Cys-Asp-Gly-Lys-Tyr-Phe-Ala-Tyr-Lys-Val-Glu-Thr-Ile-Leu-Lys-Arg-Phe-His-Ser-Met-Tyr-Gly;
   (b) Cys-Asn-Ile-Ala-Pro-Ala-Ser-Ile-Val-Ser-Arg-Asn-Ile-Val-Tyr-Thr-Arg-Ala-Gln-Pro-Asn-Gln-Asp-Ile-Ala;
   (c) Cys-Gly-Ala-Ser-Arg-Asn-Ile-Val-Tyr-Thr-Arg-Ala;
   (d) Cys-Gly-Ala-Ser-Ser-Asn-Ile-Val-Tyr-Thr-Arg-Ala; and
   (e) Asp-Thr-Phe-Glu-Gly-Ala-Pro-Ala-Pro-Ala-Cys-Gly-Ala-Ser-Arg-Asn-Ile-Val-Tyr-Thr-Arg-Ala.

12. In an immunological carrier complex including an epitope-bearing moiety coupled to a carrier, the improvement comprising using a protein comprising the amino acid sequence of rotavirus VP6 inner capsid protein as said carrier.

13. The improvement of claim 12 wherein said epitope-bearing moiety is contained on a molecule which further comprises a binding peptide portion and wherein said molecule is bound to the carrier through protein-protein interaction between said carrier and said binding peptide portion.

14. The improvement of claim 12 wherein said epitope-bearing moiety is coupled to said carrier through conventional chemical coupling.

15. The improvement of claim 12 wherein said epitope-bearing moiety is a lipid or a nucleic acid.

16. A method of forming an immunological carrier complex including an epitope-bearing moiety comprising:
   (a) providing a carrier protein comprising a rotavirus VP6 inner capsid protein amino acid sequence;
   (b) providing an epitope-bearing moiety contained in a molecule which includes a peptide portion capable of binding said carrier protein through protein-protein interaction; and
   (c) contacting said carrier protein with said molecule under conditions whereby said molecule becomes bound to said carrier protein through protein-protein interaction.

* * * * *